(12) United States Patent
Altman et al.

(10) Patent No.: US 8,172,901 B2
(45) Date of Patent: May 8, 2012

(54) PROSTHETIC DEVICE AND METHOD OF MANUFACTURING THE SAME

(75) Inventors: Gregory H. Altman, Arlington, MA (US); Enrico Mortarino, Hickory, NC (US); David J. Horan, Westfield, MA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/052,719

(22) Filed: Mar. 20, 2008

(65) Prior Publication Data

US 2008/0300683 A1 Dec. 4, 2008

Related U.S. Application Data

(60) Provisional application No. 60/919,126, filed on Mar. 20, 2007.

(51) Int. Cl.
*A61F 2/08* (2006.01)

(52) U.S. Cl. .................... 623/13.12; 623/13.11

(58) Field of Classification Search ............... 623/1.44, 623/11.11, 13.11, 13.12, 13.19
See application file for complete search history.

(56) References Cited

U.S. PATENT DOCUMENTS

| | | |
|---|---|---|
| 2,119,893 A | 6/1938 | Stark |
| 3,595,276 A | 7/1971 | Wrzesien |
| 3,613,120 A | 10/1971 | McFarland |
| 3,797,047 A | 3/1974 | Pillet |
| 3,805,300 A | 4/1974 | Tascon-Alonso et al. |
| 3,842,441 A | 10/1974 | Kaiser |
| 3,896,500 A | 7/1975 | Rambert et al. |
| 3,953,896 A | 5/1976 | Treace |
| 3,988,783 A | 11/1976 | Treace |
| 4,034,763 A | 7/1977 | Frazier |
| 4,118,842 A | 10/1978 | Norris et al. |
| 4,127,902 A | 12/1978 | Homsy |
| 4,149,277 A | 4/1979 | Bokros |
| 4,187,558 A | 2/1980 | Dahlen et al. |
| 4,209,859 A | 7/1980 | Hoffman |
| 4,246,660 A | 1/1981 | Wevers |
| 4,255,820 A | 3/1981 | Rothermel et al. |
| 4,301,551 A | 11/1981 | Dore et al. |
| 4,329,743 A | 5/1982 | Alexander et al. |
| 4,345,339 A | 8/1982 | Muller et al. |
| 4,411,027 A | 10/1983 | Alexander et al. |

(Continued)

FOREIGN PATENT DOCUMENTS

EP 0437174 A 7/1991

(Continued)

*Primary Examiner* — Thomas J Sweet
*Assistant Examiner* — Matthew Schall
(74) *Attorney, Agent, or Firm* — Stephen Donovan; Debra Condino

(57) ABSTRACT

A knitted prosthetic device has at least two knitted sections, where each knitted section has at least one row of fiber. The knitted prosthetic device also has at least one intra-articular section disposed between the at least two knitted sections. In addition, the at least one intra-articular section has at least one single continuous fiber traversing the at least one intra-articular section and the at least two knitted sections, where the at least one single continuous fiber forms a plurality of traverses extending between the at least two knitted sections. In particular, embodiments may be used as ligament prostheses by anchoring each of the at least two knitted sections to a bone section of a patient. Such embodiments may be constructed from a strong polymer, preferably, but not limited to, silk, where the polymer provides ligament support but bioresorbs as load bearing responsibilities are transferred to tissue resulting from in-growth.

99 Claims, 26 Drawing Sheets

U.S. PATENT DOCUMENTS

| | | |
|---|---|---|
| 4,455,690 A | 6/1984 | Homsy |
| 4,483,023 A | 11/1984 | Hoffman et al. |
| 4,597,766 A | 7/1986 | Hilal et al. |
| 4,605,414 A | 8/1986 | Czajka |
| 4,610,688 A | 9/1986 | Silvestrini et al. |
| 4,642,119 A | 2/1987 | Shah |
| 4,668,233 A | 5/1987 | Seedhom et al. |
| 4,713,075 A | 12/1987 | Kurland |
| 4,731,084 A | 3/1988 | Dunn et al. |
| 4,755,183 A | 7/1988 | Kenna |
| 4,759,765 A | 7/1988 | Van Kampen |
| 4,769,038 A | 9/1988 | Bendavid et al. |
| 4,773,910 A | 9/1988 | Chen et al. |
| 4,775,380 A | 10/1988 | Seedhom et al. |
| 4,776,851 A | 10/1988 | Bruchman et al. |
| 4,790,850 A | 12/1988 | Dunn et al. |
| 4,792,336 A | 12/1988 | Hlavacek et al. |
| 4,816,028 A | 3/1989 | Kapadia et al. |
| 4,828,562 A | 5/1989 | Kenna |
| 4,834,752 A | 5/1989 | Van Kampen |
| 4,851,005 A | 7/1989 | Hunt et al. |
| 4,863,471 A | 9/1989 | Mansat |
| 4,883,486 A | 11/1989 | Kapadia et al. |
| 4,917,699 A | 4/1990 | Chervitz |
| 4,917,700 A | 4/1990 | Aikins |
| 4,932,972 A | 6/1990 | Dunn et al. |
| 4,942,875 A | 7/1990 | Hlavacek et al. |
| 4,950,293 A | 8/1990 | Beacon et al. |
| 4,997,434 A | 3/1991 | Seedhom et al. |
| 5,004,474 A | 4/1991 | Fronk et al. |
| 5,024,669 A | 6/1991 | Peterson et al. |
| 5,049,155 A | 9/1991 | Bruchman et al. |
| 5,078,745 A | 1/1992 | Rhenter et al. |
| 5,092,887 A | 3/1992 | Gendler |
| 5,116,373 A | 5/1992 | Jakob et al. |
| 5,171,273 A | 12/1992 | Silver et al. |
| 5,171,274 A | 12/1992 | Fluckiger et al. |
| 5,171,505 A | 12/1992 | Lock |
| 5,192,322 A | 3/1993 | Koch et al. |
| 5,197,983 A | 3/1993 | Berman et al. |
| 5,217,495 A | 6/1993 | Kaplan et al. |
| 5,252,277 A | 10/1993 | Uy |
| 5,258,040 A | 11/1993 | Bruchman et al. |
| 5,263,984 A | 11/1993 | Li et al. |
| 5,376,118 A | 12/1994 | Kaplan et al. |
| 5,425,766 A | 6/1995 | Bowald |
| 5,456,721 A | 10/1995 | Legrand |
| 5,456,722 A | 10/1995 | McLeod et al. |
| 5,549,676 A | 8/1996 | Johnson |
| 5,595,621 A | 1/1997 | Light et al. |
| 5,800,543 A | 9/1998 | McLeod et al. |
| 5,919,232 A | 7/1999 | Chaffringeon et al. |
| 5,990,378 A | 11/1999 | Ellis |
| 6,110,207 A | 8/2000 | Eichhorn et al. |
| 6,110,590 A | 8/2000 | Zarkoob et al. |
| 6,113,623 A | 9/2000 | Sgro |
| 6,136,022 A | 10/2000 | Nunez et al. |
| 6,203,572 B1 | 3/2001 | Johnson et al. |
| 6,599,319 B2 | 7/2003 | Knudsen et al. |
| 6,602,290 B2 | 8/2003 | Esnouf et al. |
| 6,638,284 B1 | 10/2003 | Rousseau et al. |
| 6,729,356 B1 | 5/2004 | Baker et al. |
| 6,773,459 B2 | 8/2004 | Dauner et al. |
| 6,866,681 B2 | 3/2005 | Laboureau et al. |
| 6,946,003 B1 | 9/2005 | Wolowacz et al. |
| 6,966,918 B1 | 11/2005 | Schuldt-Hempe et al. |
| 6,971,252 B2 | 12/2005 | Therin et al. |
| 7,014,807 B2 | 3/2006 | O'Brien |
| 7,115,388 B2 | 10/2006 | Tsubouchi |
| 2001/0044659 A1 | 11/2001 | Laboureau et al. |
| 2002/0133229 A1 | 9/2002 | Laurencin et al. |
| 2003/0100948 A1 | 5/2003 | Goulet et al. |
| 2003/0100954 A1 | 5/2003 | Schuldt-Hempe et al. |
| 2003/0114929 A1 | 6/2003 | Knudsen et al. |
| 2003/0212456 A1 | 11/2003 | Lipchitz et al. |
| 2004/0029478 A1 | 2/2004 | Planck et al. |
| 2004/0034373 A1 | 2/2004 | Schuldt-Hempe et al. |
| 2004/0078077 A1 | 4/2004 | Binette et al. |
| 2004/0078089 A1 | 4/2004 | Ellis et al. |
| 2004/0097709 A1 | 5/2004 | Armato et al. |
| 2004/0170827 A1 | 9/2004 | Crighton |
| 2004/0199241 A1* | 10/2004 | Gravett et al. ............ 623/1.13 |
| 2004/0243235 A1 | 12/2004 | Goh et al. |
| 2004/0267362 A1 | 12/2004 | Hwang et al. |
| 2005/0021152 A1 | 1/2005 | Ogle et al. |
| 2005/0043733 A1 | 2/2005 | Eisermann et al. |
| 2005/0060033 A1 | 3/2005 | Vacanti et al. |
| 2005/0096743 A1 | 5/2005 | Schmieding et al. |
| 2005/0112349 A1 | 5/2005 | Laurencin et al. |
| 2005/0244455 A1 | 11/2005 | Greenawalt |
| 2005/0260706 A1 | 11/2005 | Kaplan et al. |
| 2005/0288797 A1 | 12/2005 | Howland |
| 2006/0095134 A1 | 5/2006 | Trieu et al. |
| 2006/0095137 A1* | 5/2006 | Chung et al. ............ 623/23.58 |

FOREIGN PATENT DOCUMENTS

| | | |
|---|---|---|
| EP | 0485986 A | 5/1992 |
| EP | 0561710 A | 9/1993 |
| EP | 1493404 A | 1/2005 |
| FR | 2755846 A | 5/1998 |
| WO | 89/01320 A | 2/1989 |
| WO | 01/52773 A1 | 7/2001 |
| WO | 02/30324 A | 4/2002 |
| WO | 2005/070340 A1 | 4/2005 |

* cited by examiner

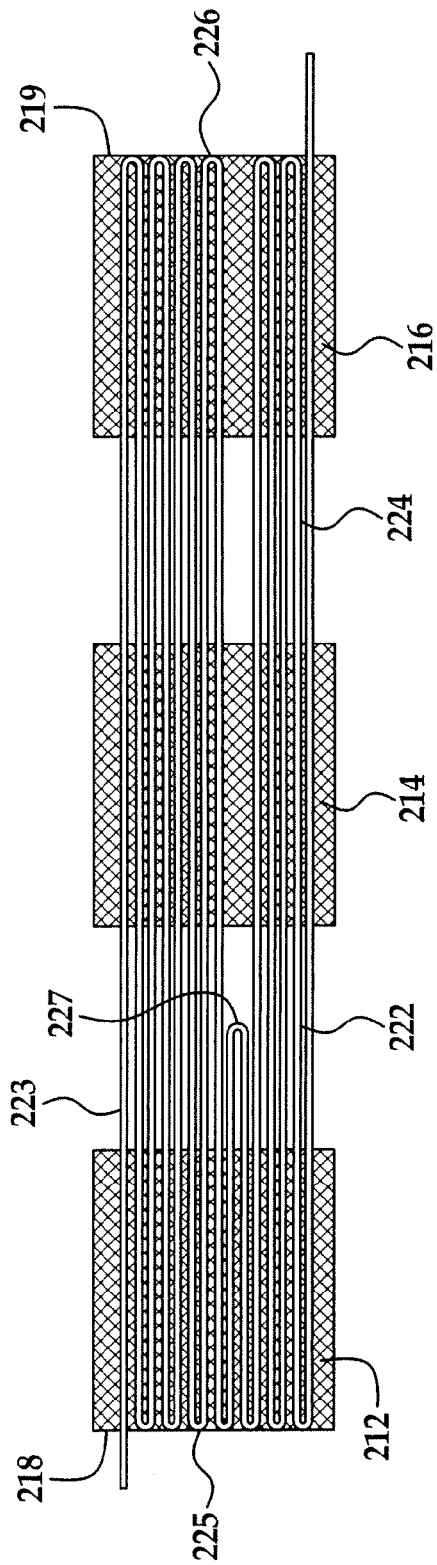
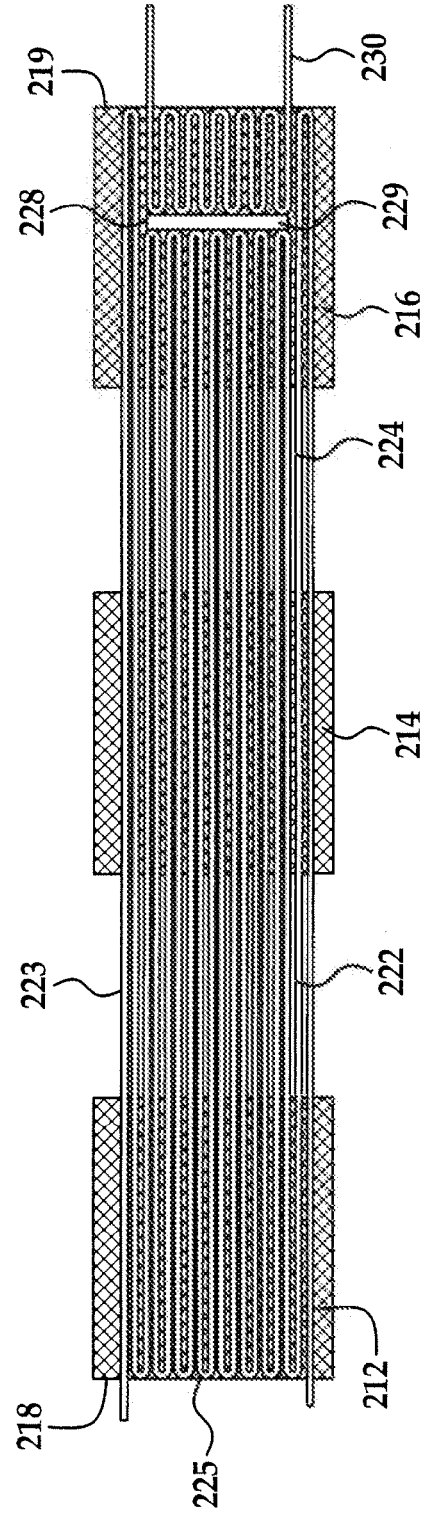
FIG. 3B
FIG. 3C

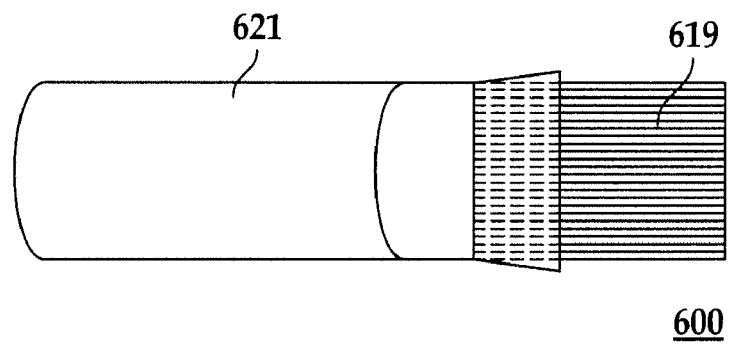
FIG. 30
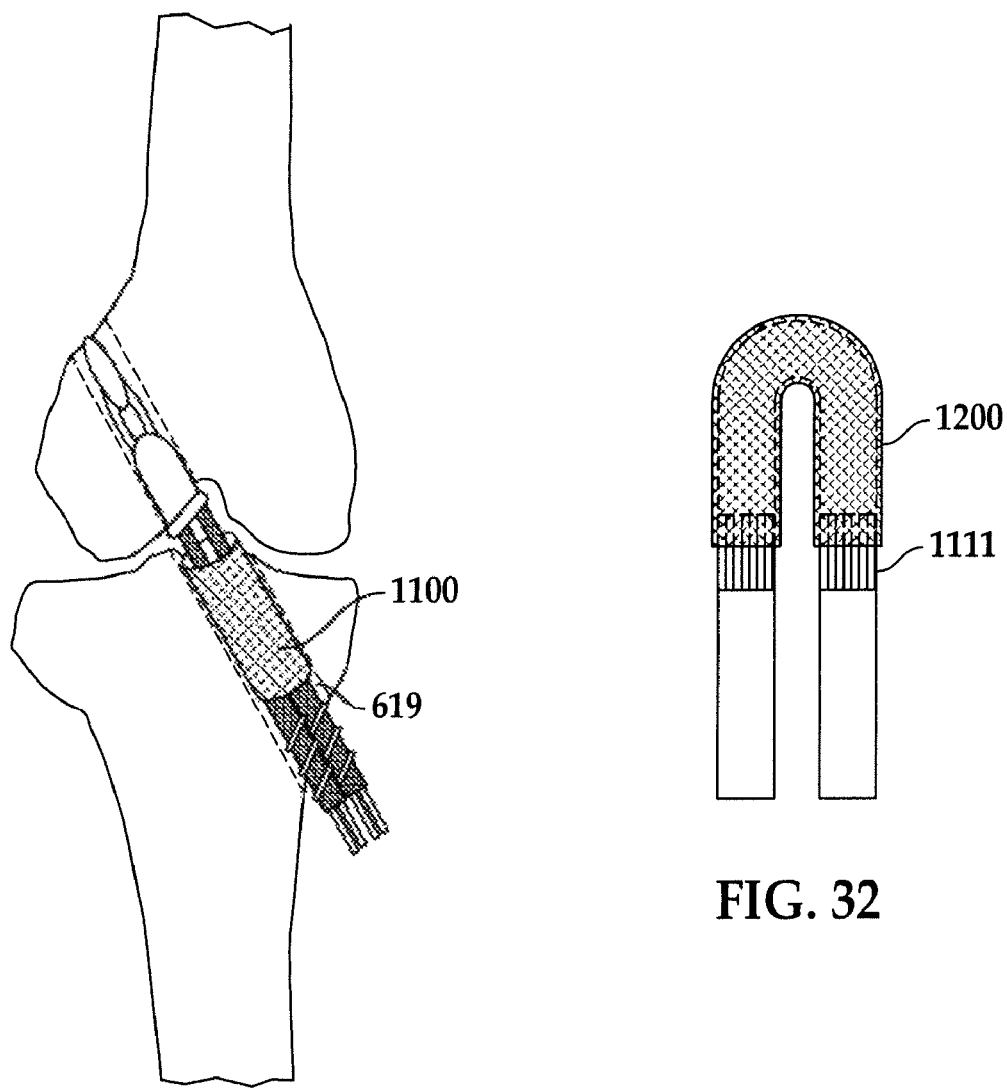
FIG. 31
FIG. 32

PROSTHETIC DEVICE AND METHOD OF MANUFACTURING THE SAME

CROSS REFERENCE TO RELATED APPLICATIONS

This application claims the benefit of U.S. Provisional Application No. 60/919,126 filed Mar. 20, 2007, the contents of which are incorporated herein by reference.

BACKGROUND OF THE INVENTION

1. Field of the Invention

The present invention relates to a prosthetic device for ligament reconstruction, and more particularly, to a fabric prosthetic device used for reconstruction of ligament tissue.

2. Description of the Related Art

Every year, hundreds of thousands of people sprain, tear, or rupture ligaments and tendons of the knee, elbow, hand, shoulder, wrist and jaw. One such ligament is the anterior cruciate ligament (ACL) of the knee. More than 200,000 people in the U.S. alone, tear or rupture their ACL each year. The ACL serves as a primary stabilizer of anterior tibial translation and as a secondary stabilizer of valgus-varus knee angulation, and is often susceptible to rupture or tear resulting from a flexion-rotation-valgus force associated with sports injuries and traffic accidents. Ruptures or tears often result in: severe limitations in mobility; pain and discomfort; and an inability to participate in sports and exercise. Failures of the ACL are classified in three categories: (1) ligamentous, in which ligament fibers pull apart due to tensile stress; (2) failure at the bone-ligament interface without bone fracture; and (3) failure at the bone-ligament interface with bone fracture at the attachment site of bone and ligament. Ligamentous failure is the most common type of ACL failure.

It is widely known that the ACL has poor healing capabilities. Total surgical replacement and reconstruction are required when the ACL suffers a significant tear or rupture. The most common practice is to reconstruct a torn ACL by substituting the torn ligament with the patient's own tissue, also known as an autograft. The middle third of the patellar tendon or the hamstring tendons are commonly used as autografts. Other options for substitute ligaments include donor tissues from a cadaver, also known as allografts, as well as synthetic grafts.

Conventionally, the techniques for reconstructing the ACL involve drilling tibial and femoral tunnels and pulling the autograft, allograft, or artificial ligament through the tunnels. The substitute ligament is then anchored to bone by a mechanical fixation device. Anchors may include the suspensory fixation, staples, as well as interference screws and cross pins. Often, the graft is folded in half to create a double bundle to more closely mimic the native human ACL. The size of the drilled bone tunnels depends on the size of the graft, which in turn depends on the strength of the graft material.

Although the use of autografts is common, the technique is disadvantageously accompanied by morbidity at the second surgery site from which the autograft is taken. For example, stress fracture of the patellar or weakness in the quadriceps muscle may occur, and a long rehabilitation period may be required. Furthermore, harvesting and preparation of autogeneous tissue prolong surgery time and cause additional trauma to the patient.

In-growth in the bone tunnels and about the device improves the device's strength and functionality over time. In addition, if sufficient in-growth does not occur, conventional devices may not be able to maintain proper flexibility, integrity, or tension in the long term.

In order to restore the stability of the knee with a replacement ligament, correct tensioning of the graft must also be established and maintained. A common mode of failure for conventional devices occurs when the devices loosen due to bone erosion and degradation around the implant site. In such cases, sufficient in-growth can fail to occur around the device within the bone tunnels. This then results in a slackening of the ligament and an eventual return to a dysfunctional knee.

Another disadvantage with conventional devices includes the release of debris from a failed ligament resulting in chronic inflammation of the joint. A further disadvantage includes osteolysis of bone, in and around the area of ligament attachment. Moreover, device abrasion may occur at the bone tunnel apertures.

SUMMARY OF THE INVENTION

In view of the foregoing, embodiments according to aspects of the present invention address the disadvantages of conventional devices and provide an improved device for reconstruction of ligament tissue.

Advantageously, embodiments provide a reconstructive or prosthetic device having multiple bundles of fibers that closely mimic the natural structure of ligament tissue, such as a native ACL, and allow for new tissue in-growth. In addition, embodiments provide sufficient flexibility to enable implementation in a large range of anatomies.

Furthermore, embodiments may be compatible with conventional anchoring systems and may be implanted into the same footprint as the native ligament tissue. Additionally, embodiments enable equal tensioning and distribute load evenly across a reconstructive device while it sustains a physiologic load. Another aspect of embodiments is the minimization of abrasion at bone tunnel apertures or elsewhere. Embodiments also endure surgical procedures without sustaining damage, such as unraveling or changes in critical dimensions, when being pulled through bone tunnels.

A particular embodiment provides a knitted prosthetic device with at least two knitted sections, where each knitted section has at least one row of fiber. The knitted prosthetic device also has at least one intra-articular section disposed between the at least two knitted sections. In addition, the at least one intra-articular section has at least one single continuous fiber traversing the at least one intra-articular section and the at least two knitted sections, where the at least one single continuous fiber forms a plurality of traverses extending between the at least two knitted sections.

Another embodiment provides a knitted prosthetic device with a plurality of knitted sections and an intra-articular section disposed between two consecutive knitted sections. The knitted sections and the intra-articular sections have at least one single continuous fiber, where the at least one single continuous fiber forms a plurality of traverses extending between at least two knitted sections.

Embodiments may have three sections, i.e. two knitted sections separated by one intra-articular section, or five sections, i.e. three knitted sections separated by two intra-articular sections. Furthermore, embodiments of a knitted prosthetic device according to the present invention may be used by anchoring each of the at least two knitted sections to a bone section of a patient. For example, embodiments may include features, such as loops and/or button holes, that accommodate device tensioning and/or a variety of fixation or anchoring devices that act to keep the prosthetic device in position.

Additionally, embodiments may be constructed from a strong polymer, preferably, but not limited to, silk, where the polymer is bioresorbable to allow substantial in-growth, both in the device itself and within and around the bone tunnels to maintain or improve the strength of the device-tissue construct over time. Embodiments employing such a polymer exist long enough in the joint to support the knee prior to tissue in-growth, but bioresorb as load bearing responsibilities are transferred over to the newly developing tissue.

Although some embodiments described herein may be specifically applied as prosthetic ligaments for reconstructing an ACL, it is understood that embodiments according to aspects of the present invention may be employed for other tendons and support structures. Still other aspects, features, and advantages of the present invention are readily apparent from the following detailed description, by illustrating a number of exemplary embodiments and implementations, including the best mode contemplated for carrying out the present invention. The present invention is also capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE FIGURES

FIGS. 3A-3C illustrate the device of FIG. 2 having different pivot points for the insertion yarn.

FIG. 30 illustrates an embodiment of a prosthetic device according to aspects of the present invention with a pocket within the knit section.

FIG. 31 illustrates an assembly of embodiment of a prosthetic device according to aspects of the present invention with a modified sock sleeve device.

FIG. 32 illustrates another embodiment of a prosthetic device according to aspects of the present invention with a modified sock sleeve device.

DETAILED DESCRIPTION OF THE PREFERRED EMBODIMENTS

Figure 1:
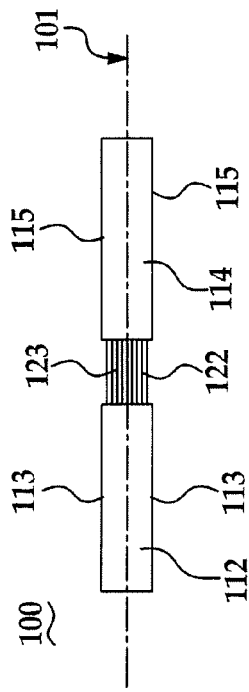
FIG. 1 illustrates an embodiment of a prosthetic device according to aspects of the present invention.

Aspects of the present invention are described herein with reference to exemplary embodiments directed to a multi-section graft, or prosthetic device, that is used to reconstruct an ACL. In particular, FIG. 1 illustrates a first embodiment of a ligament prosthesis 100 having three sections 112, 114, and 122 arranged along a longitudinal axis 101. The ligament prosthesis 100 has two knitted intra-osseous sections 112 and 114, which are separated by an intra-articular section 122. The knitted sections 112 and 114 engage the bone tunnel or anchor sections when the ligament prosthesis 100 is used to reconstruct an ACL. Meanwhile, the intra-articular section 122 acts as the ligament portion of the prosthesis 100.

Preferably, ligament prosthesis 100 is generally formed of polymers, such as protein biomaterials. In particular, embodiments may be formed from silk, such as *Bombyx mori* silkworm silk fibroin. The raw silk fibers have a natural globular protein coating known as sericin, which may have antigenic properties and must be extracted before implantation. Accordingly, the yarn is taken through an extraction process. The extraction of sericin is further described, for example, by Gregory H. Altman et al., "Silk matrix for tissue engineered anterior cruciate ligaments," BIOMATERIALS 23 (2002), pp. 4131-4141, the contents of which are incorporated herein by reference. As a result, the silk material used in the device embodiments contains substantially no sensitizing agents, in so far as can be measured or predicted with standardized biomaterials test methods.

The sericin may be extracted, or removed, from the fibroin fibers before alignment into a yarn or at a higher level in the hierarchical geometry of the fiber construct. The yarn is preferably handled at low tension, i.e. the force applied to the construct does not exceed the material's yield point during any processing step. However, if the yarn is to be employed as a non cyclic-load bearing yarn in the device, the material's yield may be exceeded. Moreover, the yarn is handled with care after the sericin is removed. Processing equipment is likewise configured to reduce abrasiveness and sharp angles in the guide fixtures that contact and direct the yarn during processing to protect the fragile fibroin fibers from damage. For example, extraction residence times may range approximately from instantaneous submersion to ten hours. In general, the extraction is slow enough to minimize damage to the exposed filaments and is determined by the configuration of the yarn being treated. When a silk fiber construct with multiple fibers organized in parallel has been extracted under these conditions, a "single" larger sericin free yarn resulted. In other words, individual fibers cannot be separated back out of the construct due to the mechanical interaction between the smaller fibroin filaments once exposed during extraction. Furthermore, due to the mechanical interplay between the sericin-free micro filaments, extraction of twisted or cabled yarns typically results in less "lively" yarns and structures. As a result, a greater degree of flexibility exists in the design of the yarns and resulting fabrics; for example, one may employ higher twist per inch (TPI) levels, which may normally create lively yarns that are difficult to form into fabrics. The added benefit of higher TPIs is the reduction in yarn and fabric stiffness, i.e. matrix elasticity may be increased.

It should be appreciated that the prothestic devices of the present invention, are not limited to the use of silk, and may be formed from a strong polymer that is capable of being knitted. In particular, the polymer is preferably bioresorbable to allow substantial in-growth, both in the device itself and within and around the bone tunnels to maintain to improve the strength of the device-tissue construct over time. The process of in-growth is discussed in further detail hereinbelow.

Moreover, embodiments may be processed with a surface treatment, which increases material hydrophilicity, biocompatibility, and handling for ease of cutting and graft pull-through, as well as anti-microbial and anti-fungal coatings. Specific examples of surface treatments include, but are not limited to, plasma modification, fibronectin, denatured collagen, collagen gels, peptides with a hydrophilic and a hydrophobic end, covalently linked proteins and peptides, physically bound and chemically stabilized peptides and gels, DNA/RNA aptamers, Peptide Nuclei Acids, avimers, modified and unmodified polysaccharide coatings, carbohydrate coating, anti-microbial coatings, anti-fungal coatings and/or phosphorylcholine coatings. The preferable concentration range for smaller proteins and peptides (in the range of 1000 kDa to 20,000 kDa) is from 0.01 μg/mg device to 100 μg/mg device. For larger proteins, a preferred concentration range is from 0.01 mg/mL to 5 mg/mL.

In general, embodiments of the present invention employ materials which that have undergone extensive biocompatibility testing in accordance with the ISO-10993 recommendations for a permanent implantable device. Generally, the materials are biocompatible, non-cytotoxic, non-irritating, non-toxic, non-pyrogenic, non-mutagenic, non-clastogenic, non-hemolytic, and non-antigenic with no evidence of sensitization or complement activation.

Figure 16:
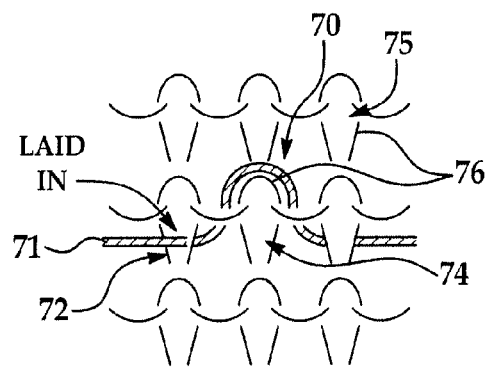
FIG. 16 illustrates an enlarged view of a tuck of a weft insertion yarn in a knitted section of a device according to aspects of the present invention.

Referring again to FIG. 1, knitted sections 112 and 114 may be formed from a weft-knitted fabric or a warp-knitted fabric. One or more single continuous weft insertion yarns 123 form the intra-articular section 122 with one or more longitudinal fibers connecting the knitted sections 112 and 114. Each of the knitted sections 112 and 114 has one or more rows, also known as courses. As shown in FIG. 16, the rows 75 may be made of a plurality of loops 76. The single continuous weft insertion yarns 123 are laid into, or received by, one or more courses in each knitted section 112 and 114 and traverse across the knitted sections 112 and 114.

A single continuous weft insertion yarn 123 in ligament prosthesis 100 refers to a single yarn that traverses the intra-articular section 122 and the knitted sections 112 and 114 to form a plurality of traverses extending between the knitted sections 112 and 114. For instance, the continuous yarn 123 may be laid in and traversed in a repetitive S-shaped or Z-shaped pattern, extending from the first knitted section to the second knitted section where it pivots and returns back to the first knitted section where it may pivot again and repeat the sequence several times. Examples of an S-shaped or Z-shaped pattern are described further below. In other words, each traverse of the single continuous yarn 123 is a continuation of the previous traverse extending in the opposite longitudinal direction. In this way, a single continuous yarn 123 with more than one traverse may connect the two knitted sections 112 and 114 and form the intra-articular section 122. The pivot points are not limited to any one location.

Of course, the ligament prosthesis 100 may contain more than one single continuous yarn 123 laid in and traversed in a repetitive pattern extending between the first knitted section and the second knitted section, thereby connecting the two knitted sections 112 and 114 with more than one traverse from more than one single continuous yarn 123. The traverses of the multiple single continuous yarns 123 may extend in the same direction, opposite directions, or any combination thereof.

The one or more single continuous yarns 123 form a plurality of parallel, non-discrete, and non-independently translatable elements which are organized into bundles, i.e. a plurality of longitudinal fibers. Advantageously, non-independently translatable fibers enable equal tensioning of all of the parallel elements of the ligament prosthesis 100 when a force acts to draw the knitted sections 112 and 114 apart.

If the ligament prosthesis 100 is a weft knitted fabric, each traverse of a single continuous yarn 123 is laid into a course of at least one knitted section and tucked, or secured, at least one time in the course. The tucking effectively locks the continuous yarn 123 into the knitted section, minimizing sliding of the yarn with respect to the knitted section, or vice versa, and minimizing any changes in the dimensions of the intra-articular section 122. One or more traverses of the single continuous yarn 123 may be laid into and/or tucked into a single course of the knitted section to form bundles of said traverses, before transitioning to the next course, or row, of the knitted section. In general, the knitted sections 112 and 114 may contain one or more rows, where each row has one or more traverses from a single continuous yarn.

Although the embodiments described herein may include a yarn tucked at each knit section, it is noted that knits that are not made on a weft knitting machine do not necessarily require that each yarn be tucked in each knit section. As such, embodiments of the present invention are not limited to those that tuck the continuous yarn at each knit section.

As further depicted in FIG. 1, the longitudinal edges 113 and 115 of knitted sections 112 and 114, respectively, are finished to prevent unraveling of the knit. In one embodiment, the edges 113 and 115 are binded off with a closed stitch. Due to this binding, no further processing, such as twisting of the prosthesis 100, is generally required. Alternatively, unraveling may be prevented by employing densely knitted sections at the edges 113 and 115. In this alternative embodiment, the edges are finished when the densely knitted sections are cut sharply.

Figure 4:
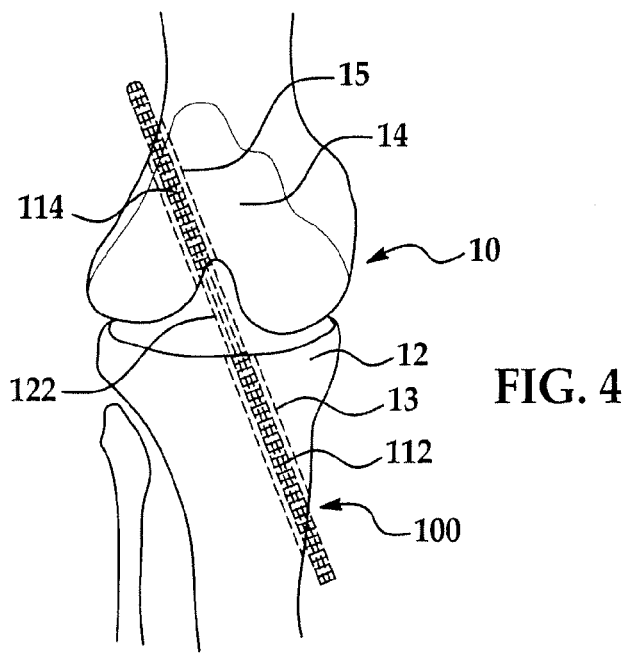
FIG. 4 illustrates the device of FIG. 1 anchored to a knee joint.

As illustrated in FIG. 4, the intra-articular section 122, in application, serves as a functional ligament when the knitted section 112 is anchored in a bone tunnel 13 at the tibial bone 12 and knitted section 114 is anchored in an opposing bone tunnel 15 at the femoral bone 14 in the knee 10. The intra-articular section 122 of the prosthesis 100 allows full functioning of the knee joint 10 while providing the necessary scaffolding and void volume for organized tissue in-growth and remodeling. As described above, advantageously, the intra-articular section 122 is formed by one or more single continuous yarns connecting the intra-osseous knitted sections 112 and 114.

Figure 2:
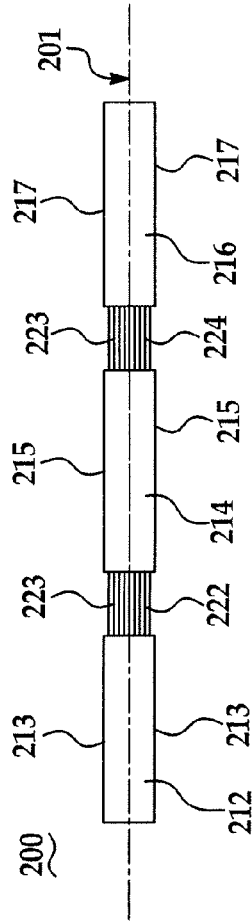
FIG. 2 illustrates another embodiment of a prosthetic device according to aspects of the present invention.

Another embodiment of a device of the present invention is shown in FIG. 2. A ligament prosthesis 200 has five sections 212, 214, 216, 222 and 224 arranged along a longitudinal axis 201. The ligament prosthesis 200 has two knitted intra-osseous end sections 212 and 216 and one knitted intra-osseous intermediate section 214. The knitted sections 212 and 214 are separated by an intra-articular section 222, and the knitted sections 214 and 216 are separated by an intra-articular section 224.

The knitted sections 212, 214, and 216 may be formed from a weft-knitted fabric or a warp-knitted fabric. As shown in FIG. 2, one or more single continuous weft insertion yarns 223 form the intra-articular sections 222 and 224 with one or more longitudinal fibers connecting the knitted sections 212, 214, and 216. Each of the knitted sections 212, 214, and 216 has one or more rows or courses. The single continuous weft insertion yarns 223 are laid into, or received by, one or more courses in each knitted section 212, 214, and 216 and traverse across the knitted sections 212, 214, and 216.

As with ligament prosthesis 100, described previously, the ligament prosthesis 200 may be formed from a strong polymer capable of being knitted, such as *Bombyx mori* silkworm silk fibroin, which has the characteristics described previously.

A single continuous weft insertion yarn 223 in ligament prosthesis 200 traverses the intra-articular sections 222 and 224, as well as the knitted sections 212, 214, and 216 to form a plurality of traverses extending between the knitted sections 212, 214, and 216. For instance, the continuous yarn 223 is laid in and traversed in a repetitive S-shaped or Z shaped pattern, extending from the first knitted end section, through the knitted intermediate section, and to the second knitted end section where it pivots and returns back through the knitted intermediate section to the first knitted end section where it may pivot again and repeat the sequence several times. Examples of an S-shaped or Z-shaped pattern are illustrated by the insertion yarn 223 in FIGS. 3A-3C, described hereinbelow. In this way, a single continuous yarn 223 with more than one traverse may connect the knitted sections 212, 214, and 216 and form the intra-articular sections 222 and 224.

Of course, the ligament prosthesis 200 may contain more than one single continuous yarn 223 laid in and traversed in a repetitive pattern extending between the first knitted end section and the second knitted end section, thereby connecting the knitted sections 212, 214, and 216 with more than one traverse from more than one single continuous yarn 223. The traverses of the multiple single continuous yarns 223 may extend in the same direction, opposite directions, or any combination thereof.

Each traverse of a single continuous yarn 223 is laid into a course of a knitted section and tucked, or secured, at least one time in the course. The tucking effectively locks the continuous yarn 223 into the knitted section, minimizing sliding of the yarn with respect to the knitted section, or vice versa, and minimizing any changes in the dimensions of the intra-articular sections 222 and 224. One or more traverses of the single continuous yarn 223 may be laid into and/or tucked into a single course of the knitted section to form bundles of said traverses, before transitioning to the next course, or row, of the knitted section. In general, the knitted sections 212, 214, and 216 may contain one or more rows, where each row has one or more traverses from a single continuous yarn.

Figure 3A:
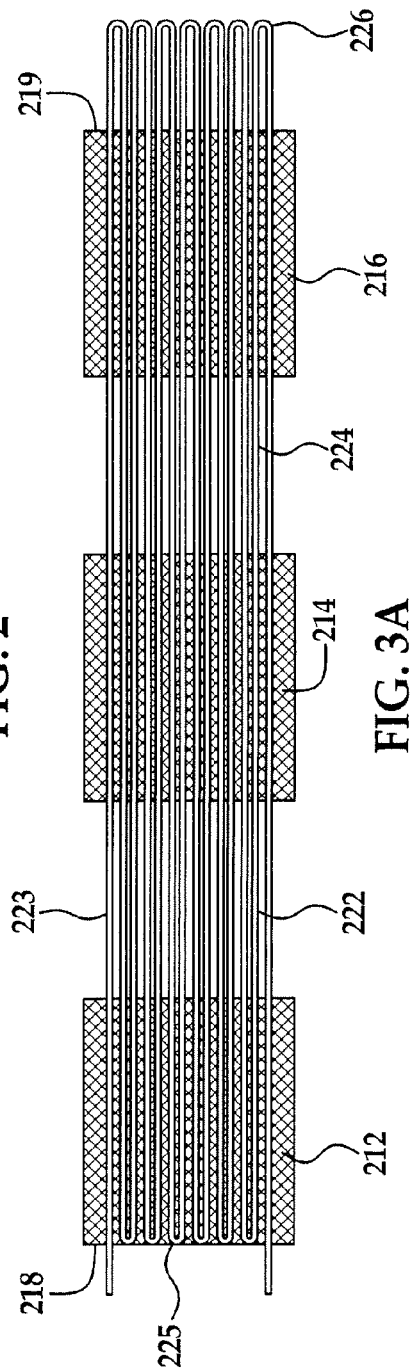

As with the ligament prosthesis 100, the pivot points for single continuous weft insertion yarn 223 are not limited to any one location. FIGS. 3A-C show embodiments of the ligament prosthesis 200 with different pivot points for the weft insertion yarn 223. FIG. 3A shows a single continuous insertion yarn 223 that has pivot points 225 at the edge 218 of knitted section 212 and pivot points 226 beyond the edge 219 of knitted section 216. The pivot points 226 in FIG. 3A form side loops, which may act as extensions for extra-articular anchoring, tensioning, or positioning of the ligament prosthesis 200. On the other hand, FIG. 3B illustrates a single continuous insertion yarn 223 with a pivot point 227 between the knitted sections 212 and 214, in addition to pivot points 225 and 226 at the edges 218 and 219 of knitted sections 212 and 216, respectively. The pivot point 227 forms an inner loop, which may provide additional fixation capability at any joint location or may be used in a third bone tunnel. Meanwhile, FIG. 3C illustrates a single continuous insertion yarn 223 with pivot points 228 at an edge of a button hole 229 in the knitted section 216. Alternatively, the button hole may be positioned perpendicular to the position illustrated in FIG. 3C and may be created between the wefts. FIG. 3C also shows that an additional insertion yarn 230 is used in combination with the insertion yarn 223 to partially shape the button hole 229, which may be employed for anchoring. The insertion yarn 230 generally pivots between the button hole 229 and the edge 219. Unlike the insertion yarn 223, the insertion yarn 230 does not traverse between the knitted sections 212, 214, and 216 to form the intra-articular sections 222 or 224. Any of the types of pivot points shown in FIGS. 3A-C may be employed in any combination with any number of the other pivot points. In addition, the pivot points may be used, in any combination, with one or more insertion yarns. Moreover, it is understood that the pivot points in embodiments of the present invention are not limited to the example pivot points illustrated in FIGS. 3A-C.

As further depicted in FIG. 2, the longitudinal edges 213, 215, and 217 of the knitted sections 212, 214, and 216, respectively, are finished to minimize unraveling of the knit. In one embodiment, the edges 213, 215, and 217 are finished with a closed stitch. Due to this binding, no further processing, such as twisting of the prosthesis 200, is generally required. Alternatively, unraveling may be prevented by employing densely knitted sections at the edges 213, 215, and 217. In this alternative embodiment, the edges are finished when the densely knitted sections are cut sharply, as later described in FIG. 14.

A graft, such as the five-section ligament prosthesis 200 was employed for ACL reconstruction in a GLP large animal study, involving 43 goats. In particular, the ligament prosthesis 200 was applied in the following manner. The right ACL of each of animal was removed and replaced in an arthroscopically-assisted procedure. The ACL was sharply excised. A guide pin was driven into the femur and antegrade drilling is performed with a 6 mm drill. The tibial tunnel was drilled under direct visualization. The five-section ligament prosthesis 200, designed to mimic hamstring grafts, was anchored extra-articularly around a post and washer on the femur. The graft was then tensioned to about 50 N, and the knee was cycled approximately 30 times before the prosthesis was fixed at the tibial bone with a spiked staple backed up with sutures around a post.

In the study, all animals were allowed to ambulate immediately after the operation. The study evaluated the five-section graft 200 for ACL replacement in the goat model at 3, 6 and 12 months after the operation. Animals were necropsied at 3, 6 and 12 months and the knees were evaluated histologically and mechanically. Additional metrics including Lachmann, x-ray, gait analysis, and comprehensive necropsies were performed.

The study showed that the animals were able to bear weight at 3, 6 and 12 months. Greater than 95% were able to return to normal gait by 6 months with maintenance at 12 months. Lachmanns show the majority of knees were clinically stable at all points. No gross cartilage damage was observed on the articular surfaces or menisci. No synovitis was observed within the synovium as a result of the device and synovial fluid was of good viscosity and color. Collagen formation and remodeling in and around the graft increased with time. Conversely, inflammation necessary for device bioresorption decreased with time. The device bioresorption rate was shown to be predictable. X-rays indicated no abnormal findings within or around the bone tunnels which was confirmed histologically with no reaction to the device observed within the tunnels with active surface modeling. Preliminary AP laxity data showed that the majority of knees were stable. Implant abrasion was observed to varying extents due to goat knee mechanics and graft placement. Single-pull-to-failure testing revealed in-growth supports increased load bearing over time.

Therefore, the results of the study indicates that the five-section ACL graft 200 supported autologous development of a mechanically robust, biologically viable ligament which stabilized the joint over a 12 month period. As such, the implant offers an ACL replacement graft without the deleterious side-effects associated with donor-site morbidity and allogenic and xenogenic grafts.

Figure 5A:
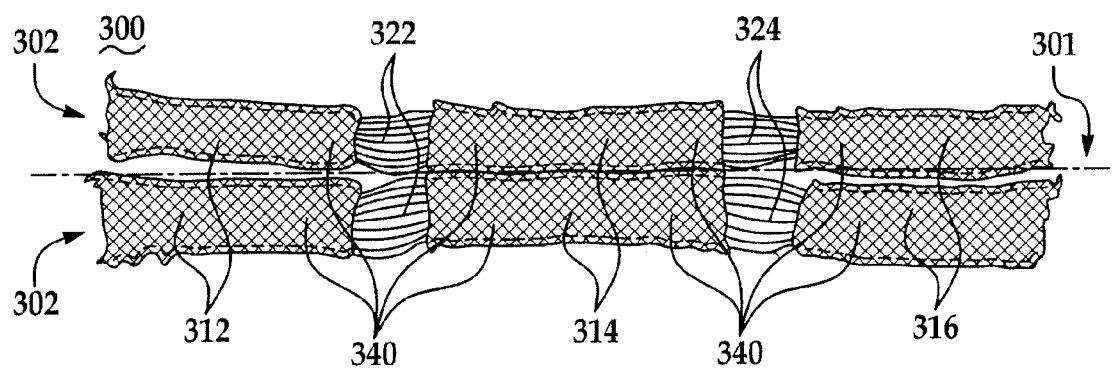
FIG. 5A illustrates another embodiment of a prosthetic device according to aspects of the present invention.

Another embodiment of a five-section ligament prosthesis is illustrated in FIG. 5A. Specifically, the ligament prosthesis 300 is a multi-section graft, having two bundles 302. Each bundle 302 has a knitted section 312, a parallel bundle intra-articular section 322, a knitted section 314, a parallel bundle intra-articular section 322, and a knitted section 316. Preferably, the two bundles 302 are joined by a knit between corresponding knitted sections 314, while corresponding knitted sections 312 and 316 are not joined. The sections 312, 314, 316, 322, and 324 are respectively similar to the sections 212, 214, 216, 222, and 224 as described above.

In addition, FIG. 5A also illustrates optional protective tubular sections 340 positioned at an edge of the knitted sections 312, 314, and 316 to minimize abrasion that occurs at these edges.

An exemplary application of a five-section ligament prosthesis is provided with reference to ligament prosthesis 300, shown in FIG. 5A. In this application, the knitted sections 312 and 316 are employed as, and may be referred to, as tibial knit sections 312 and 316, while the knitted sections 314 are employed as, and may be referred to, as femoral knit sections 314.

Figure 5B:
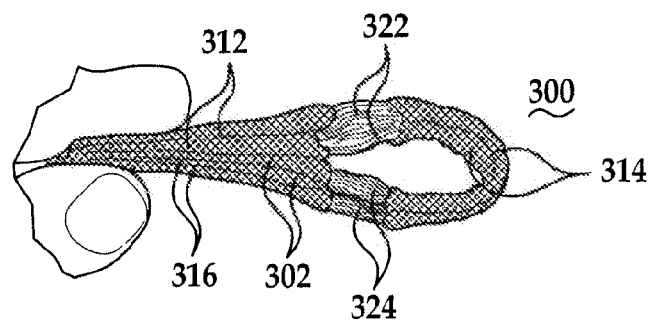
FIG. 5B illustrates the device of FIG. 5A in a folded configuration.

As shown in FIG. 5B, the ligament prosthesis 300 is folded in half along the longitudinal axis 301, and then folded transversely at the femoral sections 314. When folded in this manner, the intra-articular sections 322 and 324 of both bundles are all aligned, and a four bundle graft, or ligament prosthesis, results. In addition, the tibial knit sections 312 and 316 are aligned to serve as one section for intra-osseous anchoring, while the femoral sections 314, now folded, are aligned to serve as the opposing anchoring section.

Note that in other embodiments, such as ligament prosthesis 200, the ligament prosthesis, during application, may be folded transversely in half at the intermediate knit section, e.g. section 214, while no folding occurs along the longitudinal axis, e.g. longitudinal axis 201.

Figure 6:
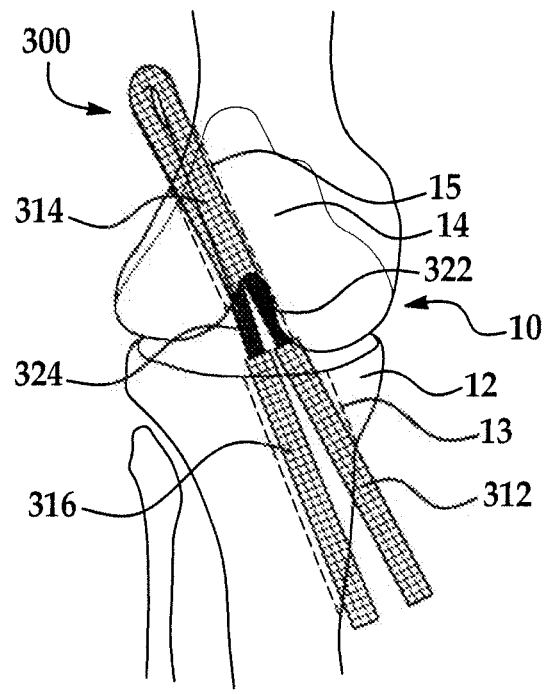
FIG. 6 illustrates the device of FIG. 5A anchored to a knee joint.

As shown in FIG. 6, the tibial sections 312 and 316 are anchored at the tibial bone 12, while the femoral sections 214 are anchored at the femoral bone 14. Advantageously, the ligament prosthesis 300 may be installed in accordance with standard surgical techniques for ACL reconstruction with a double bundle, single tunnel hamstring graft. Moreover, the ligament prosthesis 300 may be implanted with conventional anchoring devices. The ligament prosthesis 300 is compatible with standard ACL anchoring devices, including, but not limited to, the EndoButton® CL (Smith & Nephew, Mass.), or similar suspensory fixation such as the ToggleLOC™ (Arthrotek), EasyLOC™ (Arthrotek), XOButton™ (ConMed), the Intrafix (Depuy Mitek, Mass.), a post and washer, an interference screw, a pin/cross-pins, a spiked staple, a button, and sutures. Any commercially available anchor for ACL fixation is generally compatible with the ligament design.

There are two major types of fixation or anchoring devices: suspensory devices, such as the EndoButton® CL or cross-pins, provide a structure around which the graft is wrapped; and interference devices, such as the Intrafix, create an interference fit in a bone tunnel. Additionally, the ligament device itself can be used as an anchor with a press-fit within the tunnel(s).

Figure 7:
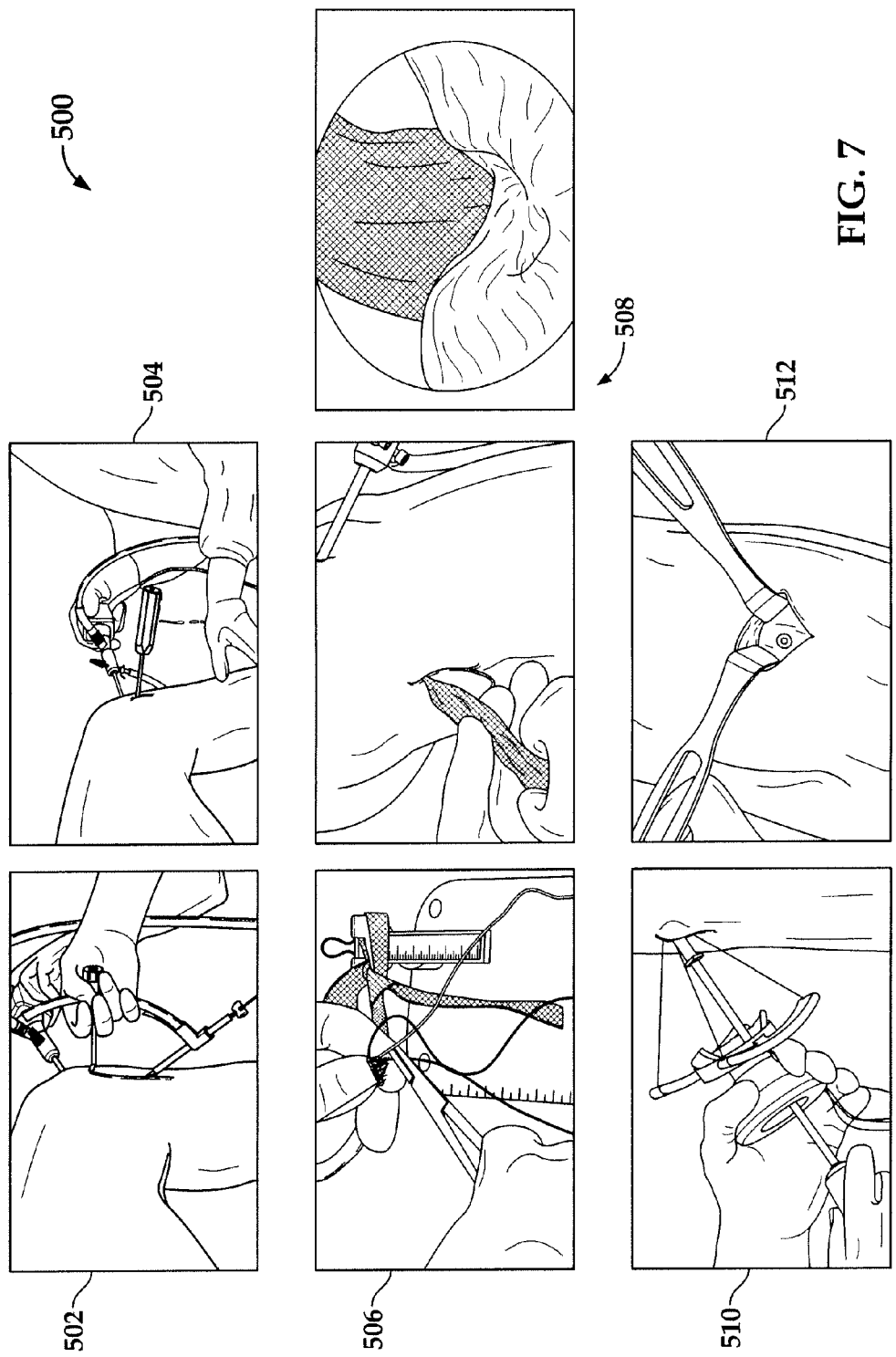
FIG. 7 illustrates exemplary steps for implementing the embodiment of FIG. 5A.

FIG. 7 illustrates steps for an exemplary technique for implanting the ligament prosthesis 300. In step 502, a single, for example, 10 mm diameter, tibial tunnel is drilled. A single femoral tunnel is drilled with a guide pin with measurement demarcations (not shown). Measurements are then taken for the femoral tunnel length and ACL length, i.e. the length between the intra-articular apertures of the tibial and femoral tunnels (not shown). The appropriate size for the ligament prosthesis 300 is then determined (not shown). In addition, the appropriate drill depth, for example, an 8 mm diameter femoral tunnel is determined to enable proper anchoring (not shown). Accordingly, as shown as step 504 in FIG. 7, a single diameter femoral tunnel is drilled to the specified depth. In step 506, the ligament prosthesis 300 is whip-stitched through the tibial knit sections 312 and 316 with a tapered needle to aid in installation and tensioning of the device. In step 508, the ligament prosthesis 300 is pulled through the tibial tunnel and into the femoral tunnel. The ligament prosthesis 300 is installed in the femur as required by the anchoring device, such as the EndoButton® CL. In step 510, the ligament prosthesis 300 is tensioned at the appropriate angle according to conventional ACL reconstruction technique. In step 512, the ligament prosthesis is fixed within the tibial tunnel using a conventional interference fixation device, such as the Intrafix. Thus, installation of the ligament prosthesis 300 may employ a combination of suspensory and interference fixation devices.

In another exemplary installation procedure, a single 8.5 mm diameter tibial tunnel may be drilled with or without a tunnel placement guide. A single 7.5 mm diameter femoral socket may be positioned transtibially or through the medial portal, according to the surgeon's preference, with or without an over-the-top guide and drilled to an appropriate depth based on total tunnel length. The total length of the tunnel and the minimum native ACL length may be measured. The appropriate size ligament device may be identified from a sizing guide. The ligament device may be prepared as would a hamstring tendon graft; the graft may be looped over standard suspensory fixation, a sock device (described in detail below) placed over the femoral section and sutures applied to the tibial ends through whip stitching or insertion of the suture through the device loops. The device may be inserted into the bone tunnels, tensioned and anchored with standard fixation.

Additionally, the ligament prosthesis may be installed by either: (i) placing the ligament device through the tibial tunnel, into the intra-articular space and then through the femoral tunnel; (ii) placing the ligament device through the femoral tunnel, into the intra-articular space and then through the tibial tunnel; or (iii) through the medial portal and into the tunnels from the intra-articular space.

The knitted sections 312, 314, 316 of the ligament prosthesis 300 serve to tension the fiber bundles that make up the intra-articular sections 322 and 324. Moreover, the knitted sections 312, 314, 316 distribute the yarns throughout the cross-section of the bone tunnels. As shown in FIG. 7, for example, the ligament prosthesis 300 is designed to fit within a single 8 mm diameter femoral tunnel and a single 10 mm diameter tibial tunnel.

Additionally, varying lengths may be employed for the ligament prosthesis 300 may be available to accommodate variations in patient anatomy.

The combined intra-articular sections 322 and 324 serve as a functional ligament when the tibial sections 312 and 316 are anchored opposite to the femoral sections 314 in the knee 10. The combined intra-articular sections 322 and 324 of the prosthesis allow full functioning of the knee joint 10 while providing the necessary scaffolding and void volume for organized tissue in-growth and remodeling. As described above, advantageously, the intra-articular section 322 is formed by one or more single continuous yarns 323 connecting the tibial sections 312 and 316. The one or more single continuous yarns 323 form a plurality of parallel, non-discrete, and non-independently translatable elements which are organized into bundles, i.e. a plurality of longitudinal fibers. Advantageously, non-independently translatable fibers enable equal tensioning of all of the parallel elements of the ligament prosthesis 300 when a force acts to draw the tibial sections 312 and 316 apart from the femoral section 314.

In an alternative application of the ligament prosthesis 300, two femoral tunnels may be drilled opposite a single tibial tunnel. As such, the aligned femoral sections 312 are anchored in one of the femoral tunnels, while the aligned femoral sections 316 are anchored in the other femoral tunnel. Meanwhile, the aligned tibial sections 314 are anchored in the single tibial tunnel. The ligament prosthesis may be implanted in any of the following configurations: (i) single tibial tunnel and single femoral tunnel, (ii) single tibial tunnel and double femoral tunnels, (iii) double tibial tunnels and single femoral tunnels, (iv) double tibial tunnels and double femoral tunnels, and (v) single tibial tunnel and over-the-top positioning on the femur.

Designed to serve as a transitory scaffold that provides immediate knee joint stabilization following surgical repair, embodiments, such as the ligament prosthesis 300, leverage the patient's own internal repair machinery and growth environment to engineer new viable ligament tissue. While conducting the body's own regenerative processes at the implant site, the transitory nature of the graft is designed to allow for tissue healing and rejuvenation as the scaffold becomes less necessary and is bioresorbed through natural and localized tissue remodeling. This approach anticipates and utilizes the body's own inflammatory, revascularization, healing, mechanical and remodeling cascades which follow graft implantation without notice to the patient.

As described above, embodiments may be may be formed from a strong polymer, such as *Bombyx mori* silkworm silk fibroin. As such, the ligament prosthesis 300 has mechanically robust parallel fiber bundles. The excellent strength of the material permits less material to be employed in the ligament prosthesis 300, while still meeting the mechanical requirements of functional ACL tissue. Correspondingly, large void volumes in excess of 50% for tissue in-growth may be created. Void volumes in excess of 50% are preferred; however, any void resulting from a device that fits properly within anatomically positioned tunnels is acceptable.

A particular embodiment of ligament prosthesis 300 may employ individual bundles 322 or 324 that are individual yarns no greater than 400 μm in diameter in order to overcome mass transport limitations in the initial post-operatively avascular environment of the knee joint-diffusion of metabolites and nutrients can support ~200 μm of cellular in-growth without active transport from a vascular network. While bundles no greater than 400 μm in diameter are preferred, ligament devices with bundles up to 2 mm in diameter are acceptable. The multi-bundle structure of the intra-articular sections 322 and 324 also promote organized tissue in-growth along the longitudinal axis of the ligament.

A variety of techniques are available for characterizing physical, mechanical, and chemical properties of embodiments of the present invention. ISO 10993 recommended biocompatibility testing and shelf-life stability studies may be also applied. Substantial pre-clinical animal trials, such as the study described previously, may be conducted to establish device biocompatibility and safety. Additionally, cadaver device implantation may be performed to determine device compatibility with standard anchors and surgical technique.

As an example, test methods and results for key parameters regarding embodiments of the ligament prosthesis are provided hereinbelow. TABLE 1 provides exemplary physical measurements including length, width and thickness for a ligament prosthesis 300. In this example, the total length and width of the ligament prosthesis 300 is approximately 170 mm by 20 mm, respectively.

TABLE 1

| | | |
|---|---|---|
| Overall Length (mm) | | 169.7 ± 1.6 |
| Length (mm) | Femur knit | 52.2 ± 2.0 |
| | Tibia knit | 40.5 ± 1.0 |
| | Intra-Articular | 18.3 ± 0.9 |
| Width (mm) | | 9.8 ± 1.2 |
| Thickness (mm) | | 1.4 ± 0.1 |

Figure 8B:
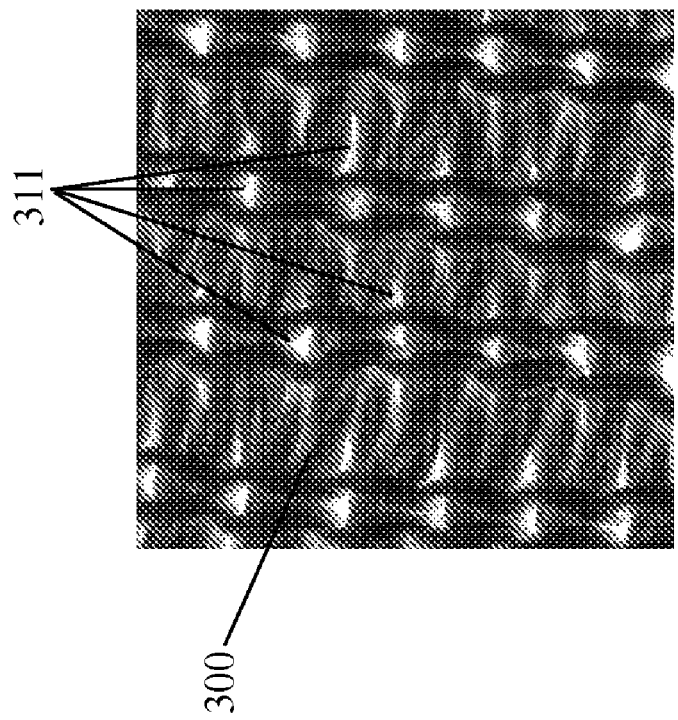
FIG. 8B illustrates pores of an embodiment of a prosthetic device according to aspects of the present invention.
Figure 8A:
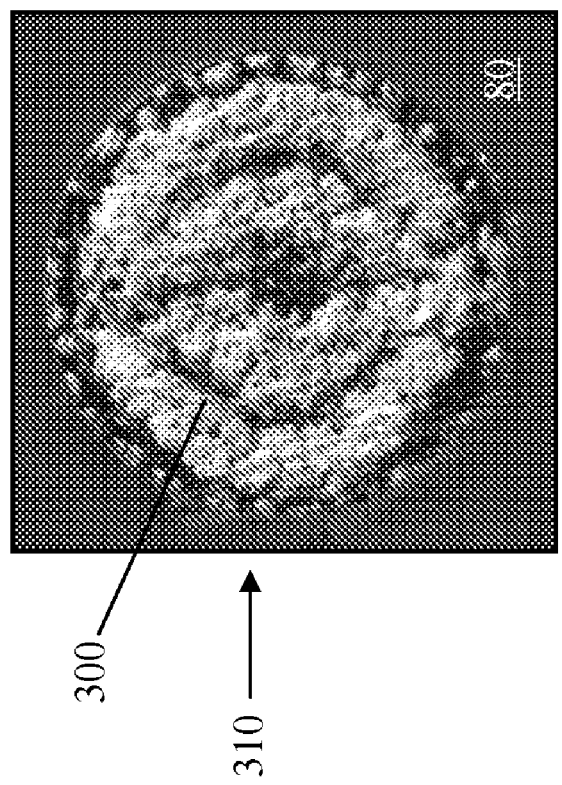
FIG. 8A illustrates a cross-sectional view of an embodiment of a prosthetic device according to aspects of the present invention.

Other physical attributes of embodiments of the present invention may also be determined. Gauge diameter may be determined for the embodiment through a graft sizing block. The prosthetic ligament 300, for example, may fit through an 8 mm diameter sizing block. Additionally, each sample may be visually inspected for color, presence of defects and distribution within an 8 mm tunnel. Such visual inspection preferably reveals that the ligament prosthetic is physically intact with no defects. Moreover, the prosthetic ligament 300 may be potted in epoxy in an 8 mm tunnel and the cross-section may be imaged using a device, such as a SZX7 Stereomicroscope (Olympus Corporation, Melville N.Y.) to determine distribution of the ligament through the tunnel. FIG. 8A illustrates an example of a ligament prosthetic 300 with a cross-section 310 that is uniform across a tunnel 80. In addition, the pore size of the embodiment may be determined histomorphometrically. FIG. 8B illustrates an example of a ligament prosthetic 300 with a minimum dimension in pores 311 that are greater than the preferable input requirement of 100 μm.

Embodiments of the present invention may also be characterized mechanically by employing tests that measure single pull to failure tensile mechanics, cyclic fatigue, and anchor pull-out. Samples of embodiments may be incubated in phosphate buffered saline (PBS) for 2±0.5 hours at 37±2° C. prior to mechanical analysis to provide characteristics in a wet environment. Mechanical testing may be performed on a servo-hydraulic Instron 8871 mechanical testing system under ambient conditions with Blue Hill and WaveMaker-Runtime Software (Instron Corporation, MA, USA).

For tensile testing, samples, following incubation, may be cut in half longitudinally and each half may be tested independently. The samples may be folded around a metal bar and anchored in a pneumatic fabric clamp. Samples may then be loaded through displacement controlled testing at a strain rate of 100% per second. Mechanical properties determined may include (1) ultimate tensile strength (UTS), (2) linear stiffness, (3) percent elongation at UTS, (3) yield strength, and (4) mode of failure. Ultimate tensile strength results may be combined from each half of the same device in order to determine overall UTS. For example, measurements for a ligament prosthesis 300 may include: a UTS of 4338±286 N; an offset yield strength of 2330±195 N; a stiffness over a 30 mm length, the native ACL length, of 721±38 N/mm; and a percent elongation at UTS of 29.7±2.5%.

Figure 9:
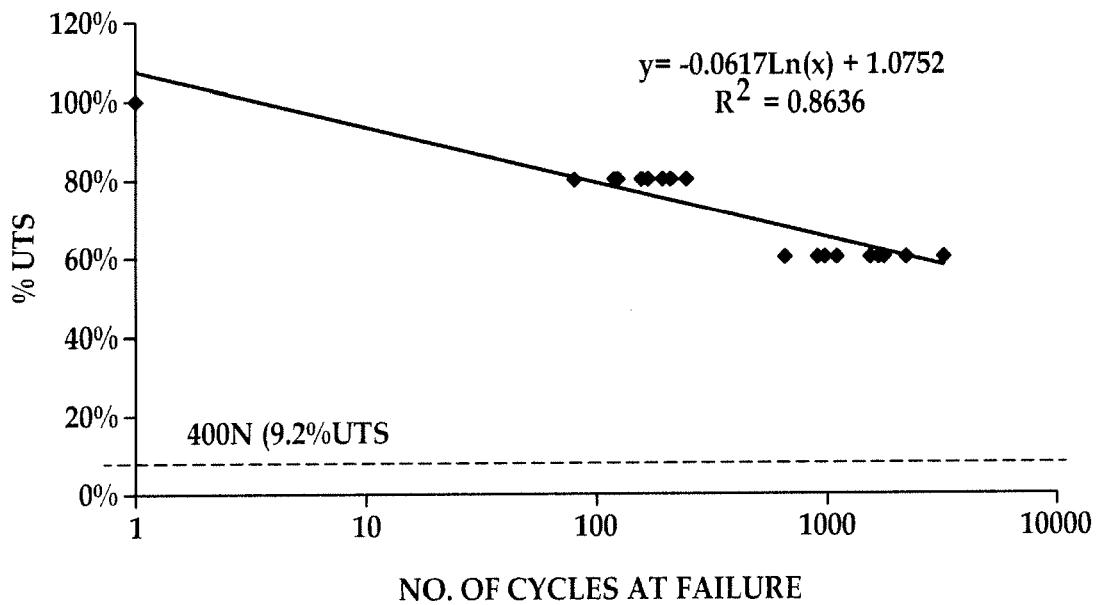
FIG. 9 illustrates a graph of the cyclic fatigue life of an embodiment of a prosthetic device according to aspects of the present invention.

For tensile cyclic fatigue testing, samples, following incubation, may be cut in half longitudinally and anchored in pneumatic fabric clamps. Samples are preferably kept wet with PBS at room temperature during cycling. Tensile sinusoidal cyclic fatigue testing may be conducted at 60% and 80% of mean UTS. As such, cycles to failure and failure mode may be determined. Cyclic fatigue life is preferably approximated for average ACL stresses in the knee joint. For instance, a prosthetic ligament 300 may fail through complete rupture after 1549±784 cycles at 60% UTS, and 173±40 cycles at 80% UTS. A logarithmic trend between the number of cycles at failure and cycling amplitude may be observed. As shown in FIG. 9, extrapolation to a 400 N load, i.e., average ACL load during walking, indicated over 8 million cycles may be completed before failure.

Anchor pull out testing may be performed with the EndoButton® CL (Smith & Nephew, Andover, Mass.) or equivalent suspensory or interference fixation for femoral fixation and the Intrafix™ (Depuy Mitek, Raynham, Mass.) or equivalent interference or suspensory fixation for tibial fixation. Biomechanical solid rigid polyurethane testing foam block (20 pcf), laminated with 2 mm foam (40 pcf) (Sawbones, Vashon, Wash. 98070), may be utilized for femoral anchor pull out testing to mimic the cortical fixation achieved with the EndoButton®. Cellular rigid polyurethane testing foam block (10 pcf) may be utilized for tibial anchor pull out testing to mimic the cancellous bone fixation achieved with the Intrafix. Accordingly, UTS and failure mode may be determined. For example, a UTS of 1130±56 N may be observed during femoral anchor pull out testing with failure occurring through EndoButton fracture. A UTS of 1202±30 N may be observed during tibial anchor pull out testing with failure occurring through sawbone failure. Tibial anchor testing of interference screws, buttons, cross-pins, staples, extraosseous post and combinations thereof may achieve pull-out strengths of 200N to 4000N.

Embodiments of the present invention may be ethylene oxide (EO) sterilized. Animal studies and biocompatibility testing, such as those conducted for prosthetic ligament 200 above, have shown no deleterious effects of EO sterilization; no results indicative of high EO residuals have been observed. In vitro characterization has shown that significant mechanical integrity is present following sterilization. Sterilization may be achieved through single lot release using an "overkill" sterilization process. Packaging may consist of a double Poly/Tyvek peel-seal pouch; 48 gauge PET/LDPE, PE0001 mated to Tyvek 1059B (Peel-Master Niles, Ill.). The overkill sterilization process requires that strategically placed biological indicators (BIs of $1.0 \times 10^6$ population) are all killed in a half exposure sterility cycle. The half exposure dwell sterilization delivers a SAL of $10^{-6}$ as preferably required for embodiments of the present invention, after which the embodiments are subjected to a full exposure sterility cycle. EO residual testing may be performed following sterilization. The maximum allowable residuals on embodiments of the present invention may be established as: 250 ppm Ethylene Oxide, 250 ppm Ethylene Chlorohydrin, and 5,000 ppm Ethylene Glycol.

The effect of EO sterilization may be determined by testing ultimate tensile strength and surface treatment concentration for the prosthetic devices prior to sterilization, after 1× sterilization, and after 2× sterilizations. Preferably, no significant difference in UTS is observed between all three groups. For instance, exemplary values for UTS for non-sterilized, 1×
sterilized, and 2× sterilized may be 100±1.5%, 101.8±5.4%,
and 100.1±4.2%, respectively.

Shelf life stability studies may also be performed on
embodiments of the present invention. In particular, testing
may be applied for devices that have been packaged and
sealed in paper-film pouches, subjected to ethylene oxide
(EO) sterilization, and stored at ambient conditions in intermittent light. Moreover, single pull to failure testing may be
applied to measure tensile strength. TABLE 2 provides
example values for such shelf life stability tests for a prosthetic ligament 200. In this case, the results indicate no significant deleterious changes in mechanical integrity were
observed following real-time ambient storage for 18 months.
As such, it may be concluded in this case that mechanical
integrity is stable for 18 months under ambient storage conditions following EO sterilization.

TABLE 2

| ACL | T = 0 months | t = 10 ± 1 months | t = 18 ± 1 months | Results |
|---|---|---|---|---|
| Ultimate Tensile Strength [N] | 1215 ± 47.5 | — | 1167 ± 29.3 | No significant decline after 18 months (p = 0.077) |

Although particular sterilization techniques are described
in detail herein, it is understood that other approaches for
sterilization may be employed, such as gamma, steam,
e-beam, chemical, ozone, vaporized hydrogen peroxide or the
like. Indeed, certain approaches, such as the "overkill" sterilization process, may be only applicable for clinical trials and
other techniques may be required for sterilizing products that
are used commercially, for example.

Figure 10:
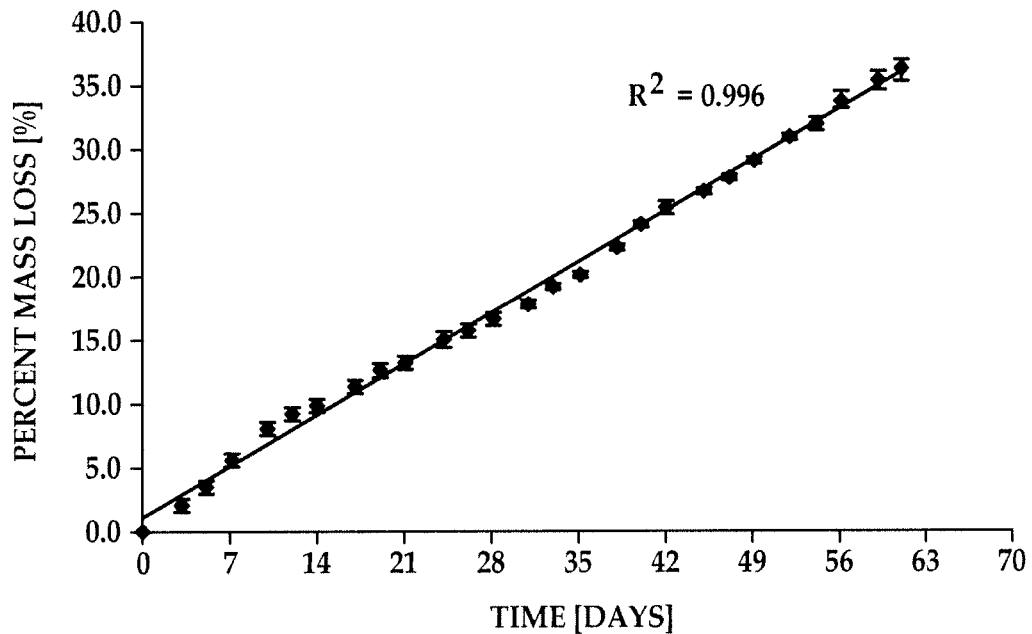
FIG. 10 illustrates a graph of the in vitro mass loss of an embodiment of a prosthetic device according to aspects of the present invention after implementation.
Figure 11:
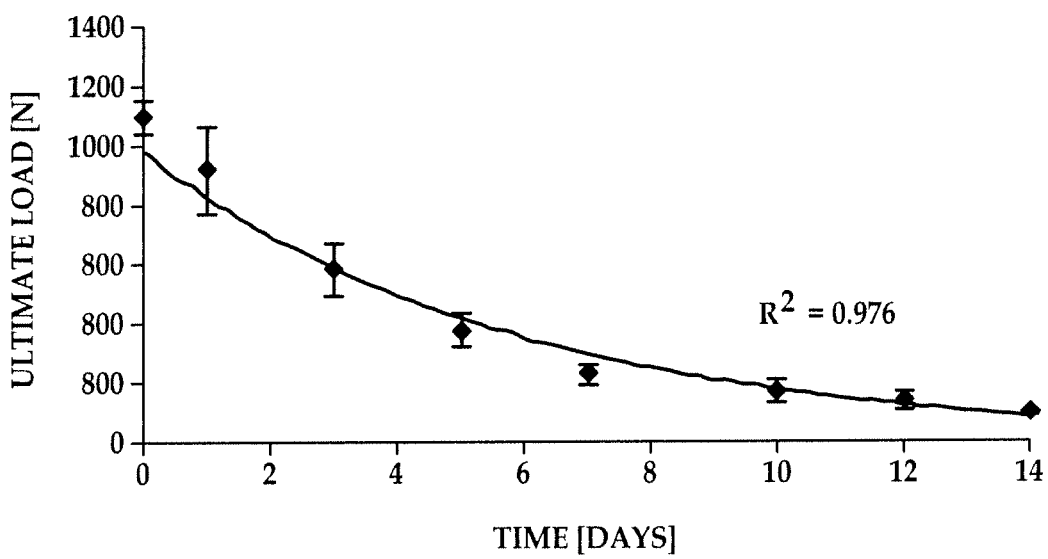
FIG. 11 illustrates a graph of in vitro strength loss of an embodiment of a prosthetic device according to aspects of the present invention after implementation.

Bench studies may be conducted to model graft bioresorption for correlation to observed trends in an in vivo model. In
particular, in-vitro bioresorption characterization may be
evaluated with embodiments that have been implanted to
replace the ACL in goats, such as the study for prosthetic
ligament 200 described previously. The embodiments may be
incubated in 0.25 mg/ml Protease XIV (Sigma, Mo.) at 37° C.
and washed 3 times per week to remove adsorbed protease.
Percent mass loss and single pull to failure mechanics of the
ligament prosthesis may determined over time. For example,
mass loss may be measured three times per week for nine
weeks. Single pull to failure may also be conducted as previously described throughout the first 14 days. FIGS. 10 and 11
illustrate sample results for the example ligament prosthesis
200. As shown in FIG. 10, in-vitro bioresorption results in
linear mass loss of the ACL grafts of approximately 36% after
61 days. The rate of bioresorption can be altered by knit and
yarn structure as well as surface treatment. Meanwhile, as
shown in FIG. 11, single pull to failure testing demonstrates
an exponential drop in strength over time in vitro and by day
14 grafts revealed a 90% reduction in ultimate tensile
strength.

Embodiments of a prosthetic device according to the
present invention may be knitted on a fine gauge crochet
knitting machine. The following is a list of crochet machines
capable of manufacturing the five-section graft used in the
study: Jakob Muller; Comez Acotronic; Zhangjiagang Kingkangda; Kyang Yhe; Ledmak Makina; Skytex Enterprise;
Valentin Rius Clapers; Zhangjiagang Victor Textile; Suzhou
Textile; Dah Heer Industrial; Jiangsu Victor; Taesin Co.;
Arushi Consultancy & Engineering; Jiangsu Hongyaun Textile; Zhangjiagang City Tianjiang; Taiwan Giu Chun; P. K.
International; Alfamatex; Wenli Weaving & Zipper; and
Ningbo Poli.

An exemplary system for making embodiments of the
present invention is described with reference to the general
five-section ligament prosthesis 200 shown in FIG. 2. In
particular, a 20 gauge Comez Acotronic Crochet machine
may be used and configured with the following specifications:
one BPO (Barre Passette Ordito) warp guide tube bar with
155 guides with one warp thread per guide, one BPO/STR
(Barre Passette Ordito Supplementare Tronic) warp guide
tube bar with 146 guides with one warp thread per guide and
two weft insertion bars, each with one guide which lay-in two
weft threads each. The warp thread is a 12 filament silk yarn,
while the weft insertion yarn is a 36 filament silk yarn, constructed in a two-step and three-step twisting process, respectively. The speed of the machine is adjusted to maintain the
stability of the knitting process and to insure consistent fabric
dimensions. For this construction, the preferred speed setting
was 75 RPM, although a speed in the range of 1 RPM to 3,000
RPM may work in this application. A 125 left/124 right
position creel is configured to feed the yarn to the machine in
a manner that prevents the crossing of yarns during operation.
The BPO/STR yarns are positioned in rows across the top, the
weft insertion yarns are positioned in the middle, and the BPO
yarns are positioned in rows across the bottom. The BPO/STR
and BPO yarn spools are unwound in derule fashion to prevent imparting a twist on the yarn during the knitting process,
while the weft yarn is unwound defile to allow rapid feeding
so as to aid operation at the desired speed. This process is not
limited to the aforementioned creel set-up as many creel
position schemes may be devised to prevent yarn cross-over
and insure proper unwind. It is also possible that yarn crossover may not inhibit the knitting process. Furthermore,
beams, such as a warp beam, or any other yarn holding/
feeding architecture may be employed.

As discussed above, embodiments may be formed from
silk, such as *Bombyx mori* silkworm silk fibroin. In a particular embodiment, for instance, the silk is a twisted yarn made
from 20 denier raw silk fibers approximately 40 to 60 μm in
diameter. Preferably, raw silk fibers of 10 to 30 denier may be
employed; however, any fiber diameters that will allow the
device bundles to be less than 2 mm and provide sufficient
strength to stabilize the knee joint when used as an ACL
device or sufficient to suspend or replace the intended tissue
structure of organ are acceptable.

In one example, for the knitted sections 212, 214, and 216,
manufacturing of the silk yarn involves two steps: i) four of
the 20 denier fibers are twisted in the counterclockwise direction (S-direction), at 6 twists per inch (tpi); and ii) three plies
from the first step are twisted together in the clockwise direction (z-direction) at 3 tpi. The result is a 12-filament yarn with
a diameter of approximately 220-323 μm.

For weft insertion yarns 223, manufacturing of the silk
yarn involves three steps: i) four of the 20 denier fibers are
twisted in the clockwise direction (z-direction) at 10 tpi; ii)
three plies from the first step are twisted together in the
counterclockwise direction (s-direction) at 19 tpi; and iii)
three plies from the second step are twisted together in the
clockwise direction (z-direction) at 9 tpi. The result is 36-filament yarn with a diameter of approximately 350-400 μm.

The yarn size for a particular type of section, i.e. knitted
sections 212, 214, and 216 or intra-articular sections 222 and
224, preferably does not vary in a given device or within a
given section of a given device. Advantageously, a substantially constant yarn size may maximize the uniformity of the
yarn's mechanical properties, e.g. stiffness, elongation, etc., throughout the sections of the ligament prosthesis. However, in other embodiments described further below, the size of yarn may be varied in particular sections of the same graft, or within any single section of a graft, in order to achieve different mechanical, physical and/or biological characteristics in different locations when implanted. For instance, areas of the graft that are closer to tunnel apertures may have larger yarn sizes in order to maximize abrasion resistance. On the other hand, areas that are farther from the bone tunnel may have smaller yarn sizes to increase flexibility. Additionally, yarn size may be varied in order to enable a certain section or sections of the graft to fit a particular type of fixation device or to achieve a press fit in a bone tunnel. Knit yarns may be different for each of the bone tunnel sections to allow the device to fit in two different diameter tunnels.

Factors that may influence the size of the yarn include, but are not limited to: ultimate tensile strength (UTS); yield strength, i.e. the point at which yarn is permanently deformed; percent elongation; fatigue and dynamic laxity (creep); bioresorption rate; transfer into and out of the graft (cells/nutrients); the ability to size the prosthetic device for implantation in the available bone tunnel; the ability to distribute fibers across a bone tunnel; and smoothness of stiffness profile, which is preferably not "stepping" as typically found in a braided yarn.

Figure 12:
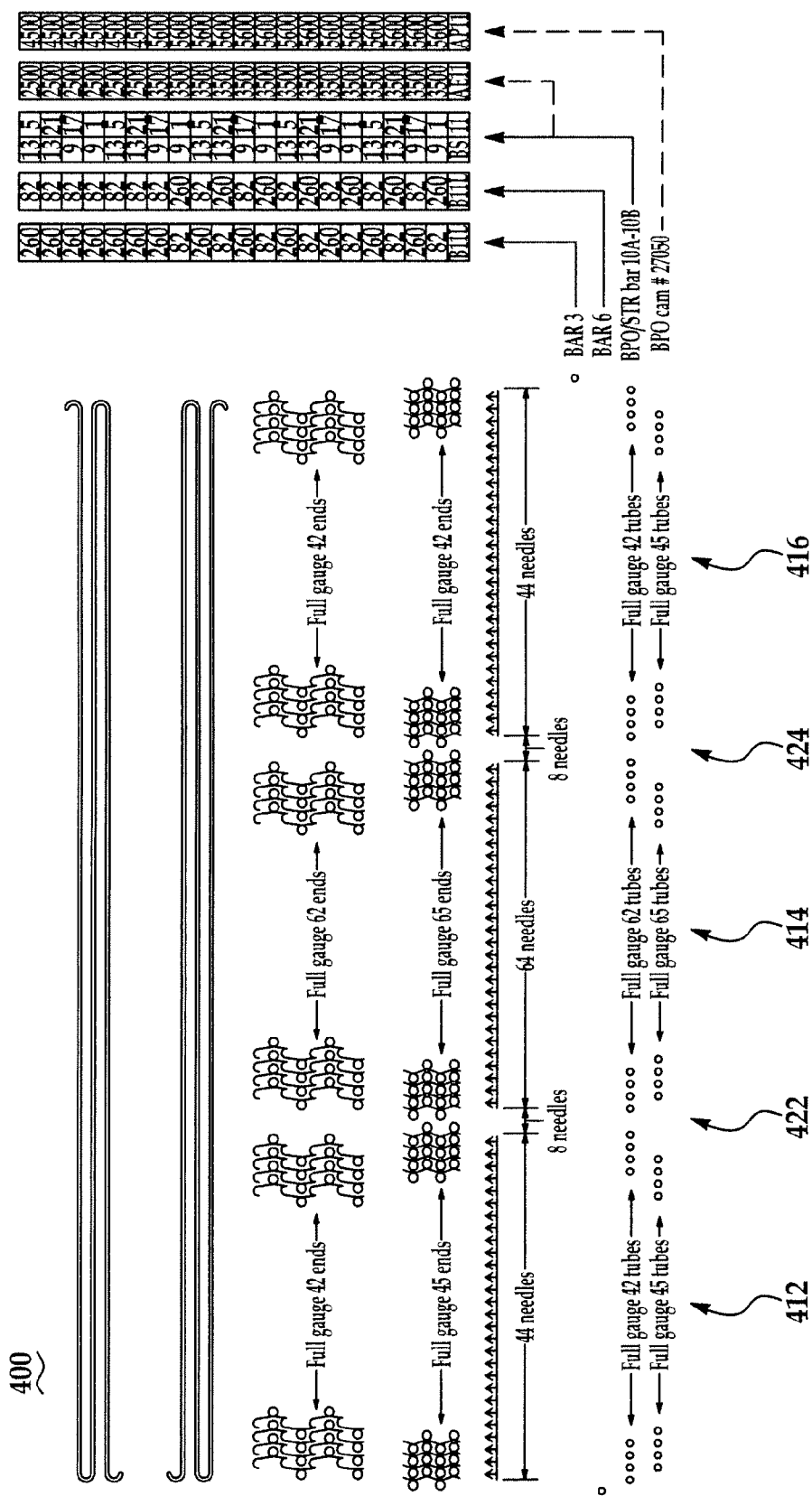
FIG. 12 illustrates a diagram of a knit pattern design for use with a system for making a prosthetic device according to the present invention.

FIG. 12 illustrates a technical diagram of a knit pattern design 400 for use with the exemplary manufacturing system described. The pattern 400 is spread across 168 needles to achieve the desired overall device length. As further shown in FIG. 13, from left to right, the device consists of three knitted sections 412, 414, and 416. The knitted sections 412 and 414 are separated by a section 422, and likewise, the knitted sections 414 and 416 are separated by a section 424. Sections 422 and 424 only include continuous inserted weft yarn. The knitted section 412 spans across 44 needles, followed by an eight needle space for section 422, followed by knitted section 414 across 64 needles, followed by an eight needle space for section 424, and followed lastly by the knitted section 416 across another 44 needles. A repeating series of 3-needle atlas stitches is performed by the BPO/STR bar with 42 guides for knitted section 412, 62 guides for knitted section 414, and 42 guides for knitted section 316. The repeating series of 3-needle atlas stitches is simultaneously stitched with 2-needle closed tricot stitches performed by the BPO bar with 45 guides for knitted section 412, 65 guides for knitted section 414, and 45 guides for knitted section 416, in order to create courses, provide dimensional stability to the prosthetic device, and enable organization of the inserted weft yarn.

Using the knit pattern design 400 of FIG. 12, the widths of sections 412, 414, and 416 may be approximately 52 mm, 79 mm and 52 mm, respectively. Embodiments of the present invention, however, are not limited to these particular dimensions. It is possible to achieve similar dimensions with a different gauge crochet machine by using a different number of needles. Moreover, the dimensions of sections 412, 414, and 416 may also be varied according to the capacities of the machines. TABLE 3 outlines the fabric widths that may be achieved using different numbers of needles on different gauge machines. It is understood that the dimensions in TABLE 3 are approximate due to the shrink factor which depends on stitch design, stitch density, and size of yarn size used.

TABLE 3

| Gauge | Needle Count | Knitting Width |
| --- | --- | --- |
| 48 | 2-5,656 | 0.53-2,997.68 mm |
| 24 | 2-2,826 | 1.06-2,995.56 mm |
| 20 | 2-2,358 | 1.27-2,994.66 mm |
| 18 | 2-2,123 | 1.41-2,993.43 mm |
| 16 | 2-1,882 | 1.59-2,992.38 mm |
| 14 | 2-1,653 | 1.81-2,991.93 mm |
| 12 | 2-1,411 | 2.12-2,991.32 mm |
| 10 | 2-1,177 | 2.54-2,989.58 mm |
| 5 | 2-586 | 5.08-2,976.88 mm |

With further reference to the exemplary knit pattern design 400 of FIG. 12, as each row or course is created, two weft bars, working in opposite directions, may each lay-in two continuous weft insertion yarns into the courses across all three sections 412, 414, and 416. Each of the four weft insertion yarns are a continuation of the same yarn from the previous row of courses. This process may be repeated to create 14 rows of courses. The result is a plurality of parallel, non-discrete and non-independently translatable yarns or elements organized into bundles for the two sections 422 and 424 between the knitted sections 412, 414, and 416.

Figure 13:
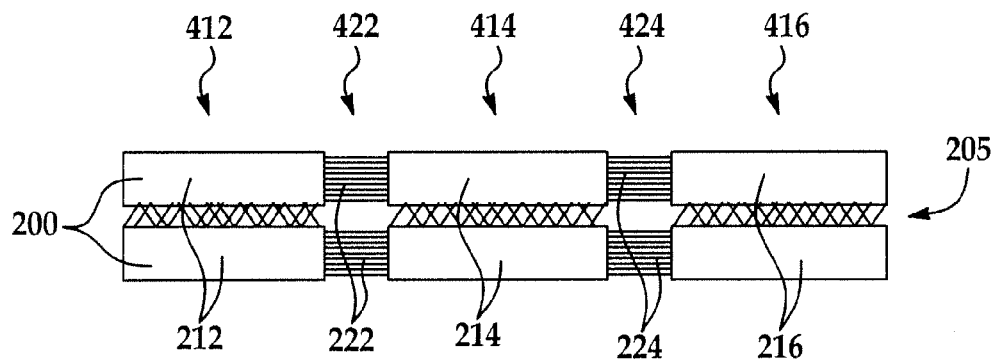
FIG. 13 illustrates a series of devices as produced by a manufacturing system according to aspects of the present invention.

Once the 14 rows have been created and one unit of a prosthetic device has been completed, the weft insertion is stopped. However, six additional courses of atlas stitches and closed tricot stitches are then performed simultaneously to separate the individual units of prosthetic devices. FIG. 13 illustrates a series of two five-section ligament prostheses 200 as produced by the manufacturing technique presently described. In particular, the two five-section ligament prostheses 200 are separated by a separation section 205 which is formed by a number of courses of atlas and closed tricot stitches.

Figure 14:
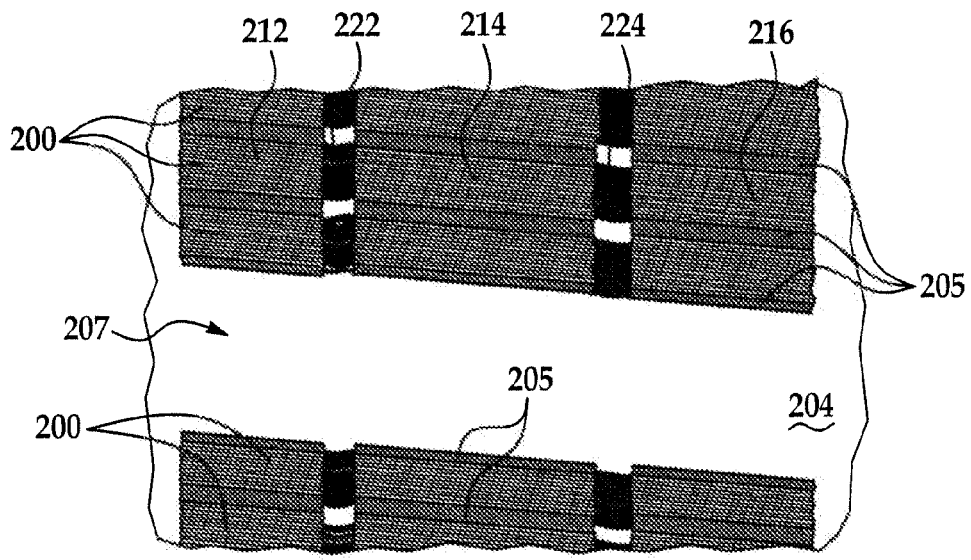
FIG. 14 illustrates a sheet with a series of prosthetic devices produced by the manufacturing system according to aspects of the present invention.

Furthermore, the stitch density is increased, e.g. from 9 to 15 stitches per cm, to create a tighter fabric in the separation section 205. This provides a mechanically locked section so that the units of prosthetic devices may be cut from the series without causing any unraveling of the knit. The result is a type of finished edge, as described previously. FIG. 14 further illustrates a series of five-section ligament prostheses 200 as produced in a sheet 204 by the manufacturing technique presently described. In particular, FIG. 14 illustrates a cut 207 performed on the sheet along a line of one of the mechanically locked courses, e.g. between the $3^{rd}$ and $4^{th}$ courses of the 6 courses of separation section 205. As described above with reference to FIG. 2, each ligament prosthesis 200 cut from the sheet has three intra-osseous knitted sections 212, 214, and 216, where sections 212 and 214 are separated by an intra-articular section 222 and sections 214 and 216 are separated by an intra-articular section 224. As such, the knitted sections 412, 414, and 416 shown in the knit pattern 400 of FIG. 12 generally correspond with the intra-osseous knitted sections 212, 214, and 216 for the ligament prostheses 200 in sheet 204. In addition, the sections 422 and 424 of knit pattern 400 correspond with the intra-articular sections 222 and 224 for the ligament prostheses 200.

The combination of atlas and closed tricot stitches described above may be preferred because it minimizes unraveling while minimizing the density of knitted construction and maximizing porosity. However, any combination of stitches created with at least two independent bars, each one forming loops over two or more adjacent, or non-adjacent, needles, may effectively create a fabric structure that does not unravel when cut. The choice of stitch combination depends on desired density, abrasion resistance, etc.

The number of courses and the number weft yarns inserted per course indicated in the present example result in 56 parallel elements organized into bundles for the intra-articular sections 222 and 224. However, the same number of parallel elements may be achieved by employing different number combinations of courses per prosthetic device and yarns per weft bar (yarns per course). For example, TABLE 4 shows different combinations that produce 56 parallel elements. TABLE 4 assumes that each weft bar employs the same number of weft yarns and that the weft insertion yarns are laid-into every course to create an even fabric across its entire width.

TABLE 4

| No. of Courses | Wefts/Bar | Wefts/Course (Wefts/Bundle) | No. of Single Continuous Weft Yarns | Total |
|---|---|---|---|---|
| 1 | 28 | 56 | 56 | 56 |
| 2 | 14 | 28 | 28 | 56 |
| 4 | 7 | 14 | 14 | 56 |
| 7 | 4 | 8 | 8 | 56 |
| 14 | 2 | 4 | 4 | 56 |
| 28 | 1 | 2 | 2 | 56 |

TABLE 4 is not an exhaustive list of combinations. For example, it is understood that varying the number of weft yarns per weft bar may result in 56 overall parallel elements in a prosthetic ligament. In one alternative embodiment of the manufacturing system, 56 parallel elements may be achieved if the one weft bar lays in 29 weft yarns and a second weft bar lays in 27 weft yarns into a prosthetic ligament with one course. Meanwhile, other exemplary embodiments may employ only one weft bar, or as many as 12 weft bars, to lay-in the yarn. Thus, many possible combinations may achieve the desired number of parallel elements in the prosthetic ligament. Ranges of possible combinations are illustrated in TABLE 5.

TABLE 5

| No. of Weft Bars | Number of Courses | Wefts/Bar | Wefts/Course | No. of Single Continuous Weft Yarns |
|---|---|---|---|---|
| 1-12 | 0-56 | 0-50 | 0-56 | 0-56 |

Figure 15:
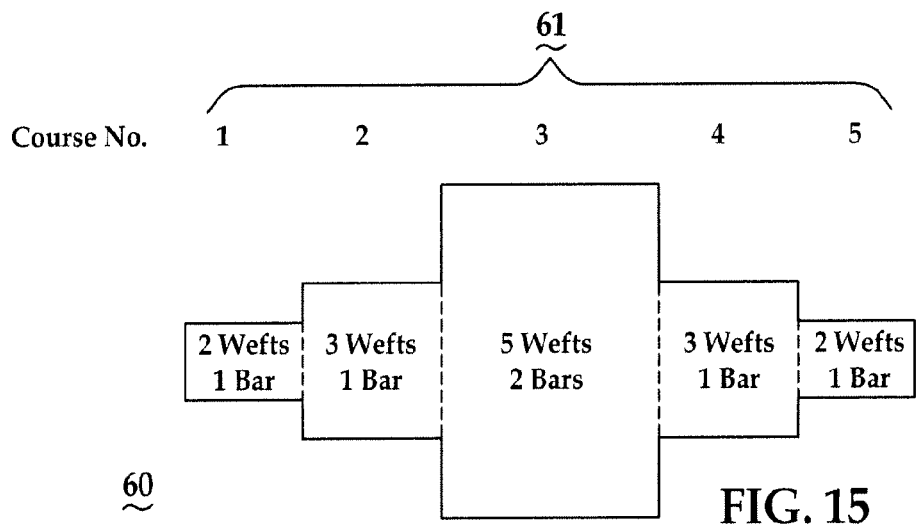
FIG. 15 illustrates a knitted fabric having five courses with varying numbers of weft insertion yarns in each course according to aspects of the present invention.

Furthermore, if more than one weft bar is employed, it may be preferable to vary the number of yarns each weft bar lays in, while varying the number of weft bars which lay in yarn in any given course. Such a configuration alters the cross-sectional geometry of the prosthetic device. For instance, FIG. 15 illustrates a cross-section of a knitted fabric 60 that has a width 61 of five courses with varying numbers of weft insertion yarns in each course. In particular, the cross-section of FIG. 15 may be achieved with two weft bars, one laying in two yarns and the other laying in three yarns. The first weft bar lays in two yarns in course number 1 and course number 2, while the second bar lays-in three yarns in course numbers 2 and 4. Both bars lay-in their yarns in the middle course number 3 for a total of five yarns.

It is understood that the range of course numbers described herein is provided merely as an example, and the number of courses is not limited to a particular range. For instance, one particular embodiment employs approximately 208 courses. The range of course numbers is from 0 to 6000 courses where the 6000 course device may be a ligament device comprised of enough single filament or greater courses to stabilize the knee joint when used as an ACL device or sufficient strength to suspend or replace the intended tissue structure or organ. For a bioresorbable ligament device, a strength of 1000 N to 5000 N is preferred. For a non-bioresorbable ligament device, a strength of 1000 N to 4000 N is preferred.

Another factor that may alter the cross-sectional geometry of a graft is the size of yarn used, as described previously. Correspondingly, another factor is the size of the needles on the manufacturing machine, e.g. a 20 gauge compound needle. Thus, the combination of yarn size, number of weft bars, and number of weft yarns per weft bar determines the diameter of the laid-in parallel elements per course. This diameter may range from 10 µm to 8,000 µm (e.g., 4 parallel elements of 2 mm diameter each).

Advantages may be associated with variations in cross-sectional geometry of a graft. For instance, more weft insertion yarns per course may be employed so that when the graft is implanted within a bone tunnel, more weft insertion yarns are present in certain regions. In particular, more weft insertion yarns may be employed at the outer end of femoral bone tunnel, where bioresorption rates tend to be higher for the graft. In addition, varying cross-section geometry may enable the weft insertion yarn bundles to be distributed more effectively within a bone tunnel diameter, depending on whether the graft is folded, rolled, etc. when implanted.

It is understood that the teachings provided for the five-section ligament prosthesis 200 can be applied to make the three-section ligament prosthesis 100, as described with reference to FIG. 1, in a similar manner. As such, TABLE 6 provides a range of dimensions as well as exemplary dimensions for the three-section ligament prosthesis 100 and the five-section ligament prosthesis 200. As shown in TABLE 6, the headings "Length of $1^{st}$ Knitted Section" and "Length of $2^{nd}$ Knitted Section" refer to the longitudinal lengths of the knitted sections 112 and 114, respectively, for the three-section ligament prosthesis 100. Similarly, "Length of $1^{st}$ Knitted Section," "Length of $2^{nd}$ Knitted Section," and "$3^{rd}$ Knitted Section" refer to the longitudinal lengths of the knitted sections 212, 214, and 216, respectively, for the five-section ligament prosthesis 200. The heading "Length of Intra-Art. Sect" refers to either the longitudinal length of the intra-articular section 122 of the ligament prosthesis 100 or the intra-articular section 222 of the ligament prosthesis 200. "Stitch density" refers to the number of stitches per centimeter and is dependent on the size of yarn used. "Wale density" refers to the size of and number of needles per unit length and depends on the gauge of the machine used.

TABLE 6

| | Length of $1^{st}$ Knitted Section | Length of $2^{nd}$ Knitted Section | Length of $3^{rd}$ Knitted Section | Length of Intra-Art. Section | Stitch Density | Wale Density |
|---|---|---|---|---|---|---|
| Range of values for 3-section | 0.5 mm-50 cm | 0.5 mm-50 cm | N/A | 0-50 cm | 1-35 stitches/cm | 5-50 gauge |

TABLE 6-continued

|  | Length of 1st Knitted Section | Length of 2nd Knitted Section | Length of 3rd Knitted Section | Length of Intra-Art. Section | Stitch Density | Wale Density |
|---|---|---|---|---|---|---|
| Range of values for 5-section | 0.5 mm-50 cm | 0.5 mm-50 cm | 0.5 mm-50 cm | 0-50 cm | 1-35 stitches/cm | 5-50 gauge |
| Example values for 3-section | 52 mm | 52 mm | N/A | 11 mm | 9 stitches/cm | 20 |
| Example values for 5-section | 52 mm | 79 mm | 52 mm | 11 mm | 9 stitches/cm | 20 |

Although the three-section ligament prosthesis 100 or the five-section ligament prosthesis 200 may be preferable for certain applications, the present invention is not limited these particular embodiments. Accordingly, embodiments may have any number of knitted sections, where one or more single continuous weft insertion yarns are laid into the knitted sections and form a plurality of longitudinal elements separating the knitted sections.

Figure 17:
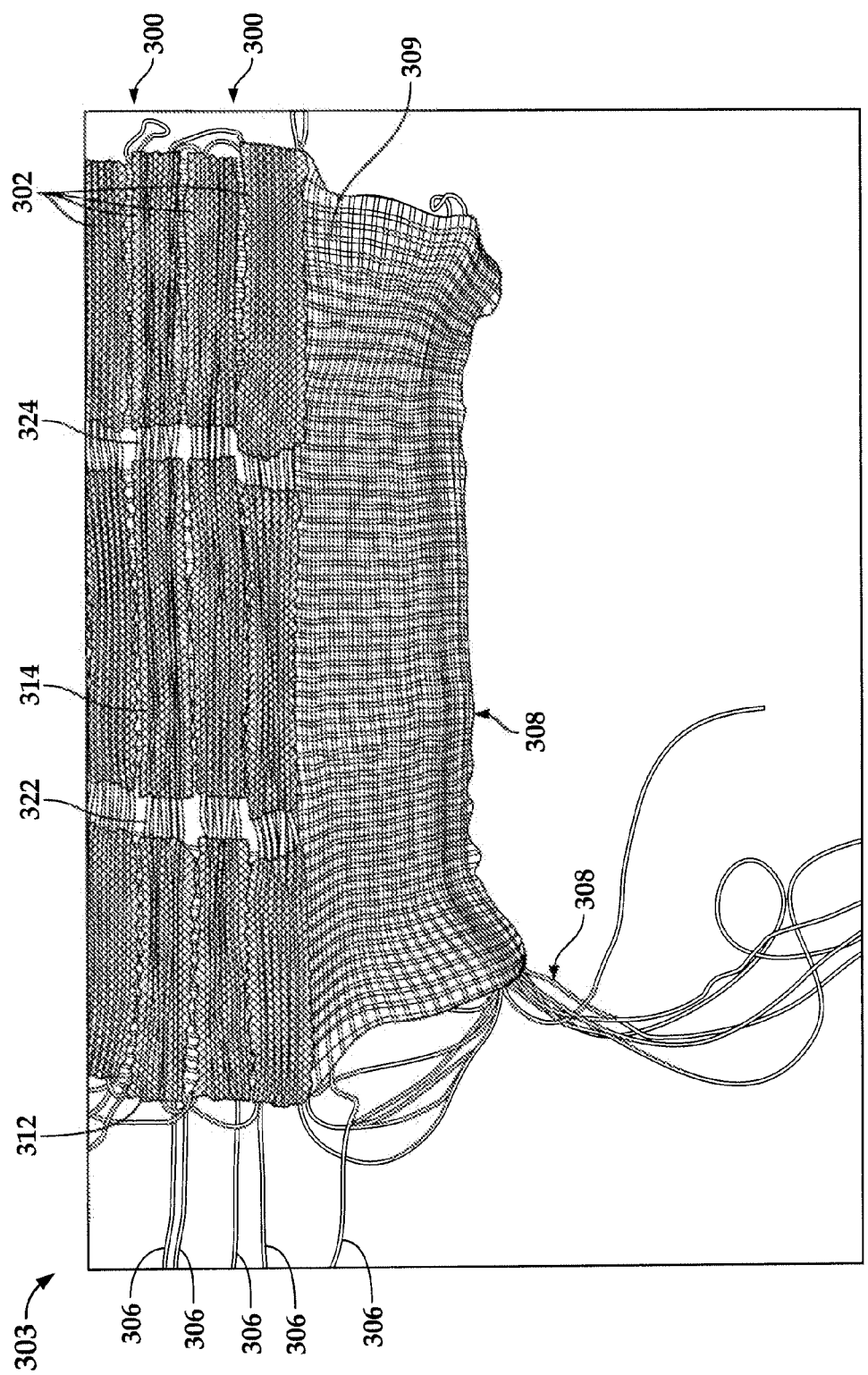
FIG. 17 illustrates a knitted sheet with a series of five-section ligament prostheses produced according to an alternative knit pattern design.

FIG. 17 illustrates a sheet 203 with a series of five-section ligament prostheses 200 which is produced according to an alternative knit pattern design. As described with reference to FIG. 2, each five-section ligament prosthesis has three knitted sections 212, 214, and 216, which are separated by intra-articular sections 222 and 224 formed by one or more single continuous yarns laid into the knitted sections 212, 214, and 216. This alternative knit design provides each ligament prosthesis 200 with closed edges on all sides. Rather than cutting the mechanically locked section according to the technique of FIG. 14, a "draw-thread" method may be employed to separate the units of the ligament prosthesis from the series after knitting. This approach involves tucking the single continuous yarns in one or more places as they traverse each knitted section in order to lock the knitted sections permanently into their respective locations and to prevent any sliding of the knit sections during implementation.

The alternative knit pattern design of FIG. 17 may be knitted on a 16 gauge Shima Seiki SES122si flat bed knitting machine configured with Intarsia yarn guides. In particular, FIG. 17 illustrates ligament prosthesis 300 described previously. The machine is equipped with a sinker system to hold previously knitted rows down and out of the way during knitting of the successive row, enabling much higher stitch densities. The pull down system of the machine includes a comb, a sub-roller and a main roller. Seven yarn guides are used in total and positioned to keep them as close to the center of the guide rails as possible. Though the guides may be positioned at any point along any of the eight parallel rails of the machine, keeping them closer to the center ensures greater knitting stability.

Initially, referring to the actual guide numbers on machine, Guide 8 of the machine is set up with SSUPY yarn (Shima Start Up Yarn) 308, as shown in FIG. 17. The SSUPY yarn 308 spans the correct number of needles determining the width of the product. Due to its elastic qualities, SSUPY yarn 308 aids the pull down system, providing the correct comb tension throughout the start-up process. Guide 7 is set up with start-up, or waste, yarn, which provides sufficient knitted fabric for the roller system to engage and to hold the product in tension as it is knitted, without damaging the actual knitted product. The waste yarn section 309 is illustrated by FIG. 17. Guides 2, 3 and 4 are set up with twisted 12 filament silk yarn, which is delivered to knit, from left to right, the knitted sections 312, 314, and 316 of each ligament prosthesis 300. Guide 5 is set up with twisted 36 filament silk insertion yarn, which is laid in continuously across the knitted sections 312, 314, and 316 and forms the intra-articular sections 322 and 324 which separate the knitted sections 312, 314, and 316.

Guide 6 is set up with a "draw thread" yarn, which is looped in between the waste yarn and the first unit of the ligament prosthesis, and in between successive units. Accordingly, pulling the draw thread 306 separates each unit from the others. As described previously, a unit of the ligament prosthesis 300 includes two bundles 302, each having knitted sections 312, 314, and 316 as well as intra-articular sections 322 and 324. Therefore, FIG. 17 illustrates a series of four bundles 302 making up two units of ligament prosthesis 300. Accordingly, the draw threads 306 between every other bundle 302 are used to completely separate each unit of ligament prosthesis 300. As also described previously, the bundles 302 are preferably joined at the intermediate, or femoral, section 314, while the end, or femoral sections, 312 and 316 are not joined. As such, the draw threads 306 may be employed to separate adjacent tibial sections 312 and 316 between every bundle 302, while only separating adjacent tibial sections 314 between every other bundle 302. In this way, every other bundle 302 is joined by femoral sections 314 to form preferred embodiments of the ligament prosthesis 300.

TABLE 7 provides the details of the Intarsia yarn guide set up, in order from left to right. The yarn supplied to each Intarsia guide is measured out by a digitally controlled stitch cam. The length of the knit loops is adjustable to 10 μm and the cam continually adjusts the yarn unwind so that the length of each knit loop in every row remains consistent throughout the entire product.

TABLE 7

| Guide 8 | Guide 7 | Guide 2 | Guide 3 | Guide 4 | Guide 5 | Guide 6 |
|---|---|---|---|---|---|---|
| SSUPY | Waste Yarn | 12t for Section 312 | 12t for Section 314 | 12t for Section 316 | 36t Insertion Yarn | "Draw Thread" |

The alternative knit pattern for the five-section ligament prosthesis is performed on the flat bed knitter. After the SSUPY yarn 308 is hooked on the appropriate needles and grabbed by the comb, waste fabric 309 is knitted in tubular single jersey knits from the waste yarn across several rows. Towards the end of the waste fabric 309, a row of waste yarn is laid in ½ gauge tubular single jersey stitches, after which all front stitches are transferred to the back needle bed. One course of tubular single jersey knits are made with the waste yarn, followed by two more courses with the "draw-thread" yarn. Next, the knit loops in the area of sections 312 and 314 are transferred to the front needle bed. The machine then carries in Guide 4 and transfers the knit loops in the area of section 314 to the back needle bed. Next, the machine carries in Guide 3 and transfers the knit loops in the area of section 312 to the back needle bed. Now all three 12 filament yarn guides, Guides 2, 3 and 4, are in position to create the three knitted sections 312, 314, and 316. One course of double jersey stitches is performed in each section, followed by two courses of single jerseys on the front needle bed and one more single jersey on the back needle bed. Next, two courses in ½ gauge are performed to create an interlock. The interlock knit loops are held on the needles while the 36t insertion yarn is laid along the width of the two courses of the interlock from left to right and back again across all three knitted sections and the spaces in between for a total of eight traverses. During the course of each traverse, the insertion yarn is "tucked," or pulled in and held by a needle on either the front or back needle bed, so that after the eight traverses and the interlock is released, the tucked portions of the 36t yarn are secured along with the loops 76 of the interlock. FIG. 16 illustrates a tuck 70, in which a 36 filament weft yarn 71, from left to right, is laid into one interlock 72 and is tucked with the loop 76 of the next interlock 74.

One exemplary technique for tucking the insertion yarn in each ligament prosthesis 300 may be achieved in the following manner. From left to right, starting in section 312, the insertion yarn is immediately tucked by a back needle, and several needles later (approximately 5-20 needles), tucked by a front needle. A few needles later (approximately 1-5 needles), it is tucked again to a front needle, for a total of three tucks in section 312. The insertion yarn lays freely across the separation between sections 312 and 314. The insertion yarn is laid-in to section 314. The insertion yarn lays freely across the separation between sections 314 and 316. Once the insertion yarn enters section 316, the insertion yarn is tucked by a back needle twice in a short distance (in a mirror image to section 312 described above). Then, after spanning section 316, the yarn is front tucked by the last needle before the yarn guide reverses and traverses right to left back across to section 312. The insertion yarn is tucked in a similar fashion as the previous traverse, except that the front and back tucks are reversed.

It is noted that tucking may affect the ability to distribute load evenly across the continuous weft yarn as the tuck acts as an anchor point. Hence, it may advantageous to limit the amount of tucks. For instance, a minimum of two tucks may be employed in sections 312 and 316, i.e. each tibial section, while no tucks are employed in section 314, i.e. the femoral section. This technique minimizes sliding by each knitted section while also enabling even tensioning.

Further describing the alternative knit pattern design for the five-section ligament prosthesis, two new courses are knitted to create the next interlock after eight traverses of the insertion yarn. This fully captures the previous eight traverses of insertion yarn, while providing a bed for the next eight traverses which are laid in and tucked in a similar fashion. This process is repeated to create eight series of interlocks, each with eight organized, parallel traverses, or bundles, of insertion yarns.

The alternative knit pattern concludes with a "bind-off" row for each ligament prosthesis 300. Starting from the farthest left in section 312, an exemplary bind-off technique transfers a knit loop from the back needle bed to the opposite needle on the front bed. A knit loop is then laid onto the vacated needle on the back bed with the draw thread. The back bed is then racked and the knit loop on the front needle is transferred to the back bed one needle to the right. The sequence is repeated across all three knitted sections 312, 314, and 316. Accordingly, each five-section ligament prosthesis 300 is successfully closed off with a finished edge and can be simply detached from the other units with the draw-thread.

It is understood that the teachings provided for this alternative knit pattern can be applied to make the three-section ligament prosthesis 100, as described with reference to FIG. 1. As such, TABLE 8 provides a range of dimensions as well as exemplary dimensions for the three-section ligament prosthesis 100 and the five-section ligament prosthesis 300 when employing the alternative knit pattern design. As shown in TABLE 8, the headings "Length of $1^{st}$ Knitted Section" and "Length of $2^{nd}$ Knitted Section" refer to the longitudinal lengths of the knitted sections 112 and 114, respectively, for the three-section ligament prosthesis 100. Similarly, "Length of $1^{st}$ Knitted Section," "Length of $2^{nd}$ Knitted Section," and "$3^{rd}$ Knitted Section" refer to the longitudinal lengths of the knitted sections 312, 314, and 316, respectively, for the five-section ligament prosthesis 300. The heading "Length of Intra-Art. Sect" refers to either the longitudinal length of the intra-articular section 122 of the ligament prosthesis 100 or the intra-articular sections 322 and 324 of the ligament prosthesis 300.

TABLE 8

|  | Length of $1^{st}$ Knitted Section | Length of $2^{nd}$ Knitted Section | Length of $3^{rd}$ Knitted Section | Length of Intra-Art. Section | Knit Loop Length |
| --- | --- | --- | --- | --- | --- |
| Range of values for 3-section | 0.5 mm-50 cm | 0.5 mm-50 cm | N/A | 0-50 cm | 0.75 mm-7.10 mm |
| Range of values for 5-section | 0.5 mm-50 cm | 0.5 mm-50 cm | 0.5 mm-50 cm | 0-50 cm | 0.75 mm-7.10 mm |
| Example values for 3-section | 40 mm | 40 mm | N/A | 15 mm | 3-4 mm |
| Example values for 5-section | 40 mm | 56 mm | 40 mm | 15 mm | 3-4 mm |

As discussed with reference to FIG. 5A, optional tubular sections 340 may be employed at an edge of the knitted sections 312, 314, and 316 to minimize abrasion that occurs at these edges. The tubular sections 340 may be formed from single jersey stitches. Alternatively, half cardigan stitches may be used. Both the single jersey stitch and the half cardigan stitch create a section of fabric with a high stitch density. However, the single jersey may be preferable due to its higher shrink factor (reduction in the width after the stitches are dropped from the needles), which increases the stitch density and provides better abrasion resistance.

Figure 18A:
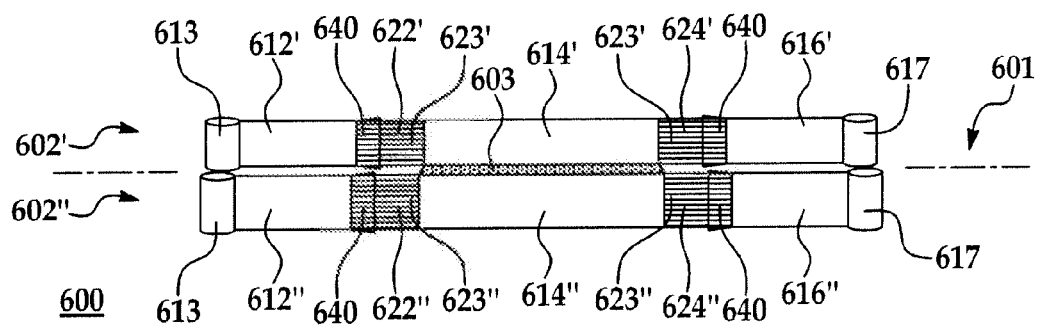
FIG. 18A illustrates yet another embodiment of a prosthetic device according to aspects of the present invention
Figure 18B:
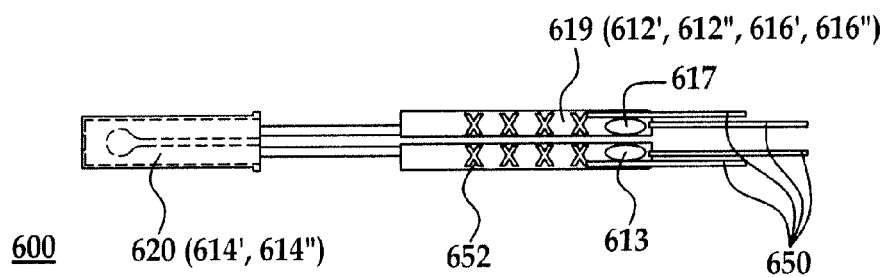
FIG. 18B illustrates the device of FIG. 18A in a folded configuration
Figure 18C:
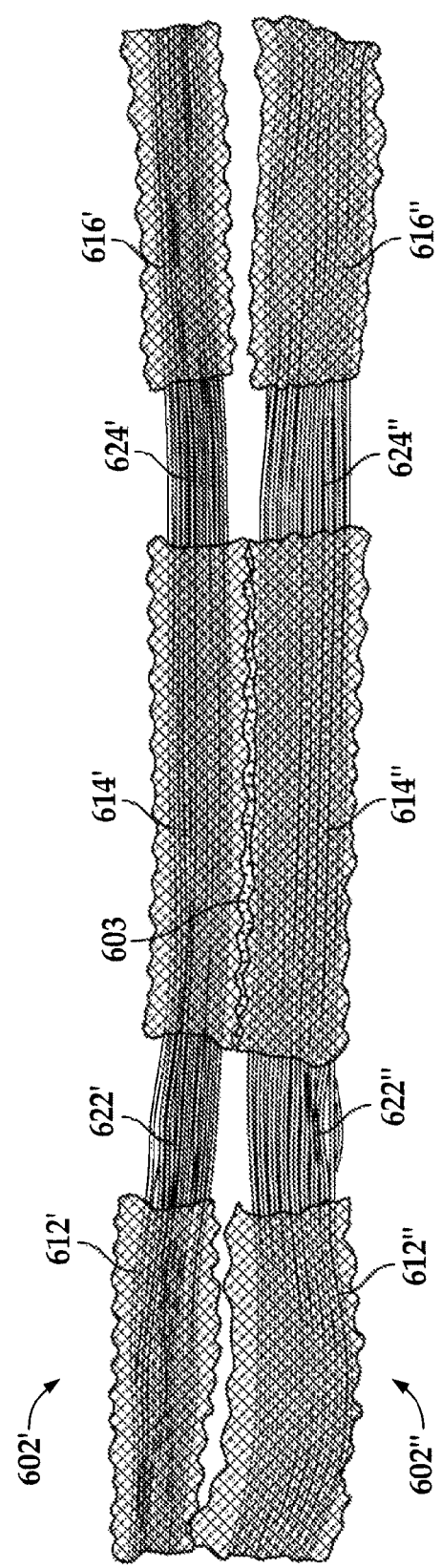
FIG. 18C illustrates the device of FIG. 18A

Another embodiment of a five-section ligament prosthesis is illustrated in FIGS. 18A and 18C. Specifically, the ligament prosthesis 600 is a multi-section graft, having two bundles 602' and 602". The bundle 602' has, in series, a first knitted section 612', a first intra-articular section 622', a second knitted section 614', a second intra-articular section 624', and a third knitted section 616'. Similarly, the bundle 602" has, in series, a first knitted section 612", a first intra-articular section 622", a second knitted section 614", a second intra-articular section 624", and a third knitted section 616". The two bundles 602' and 602" are joined by a connecting knit section 603 between corresponding knitted sections 614' and 614", while corresponding knitted sections 612'/612" and 616'/616" are not joined.

Figure 27A:
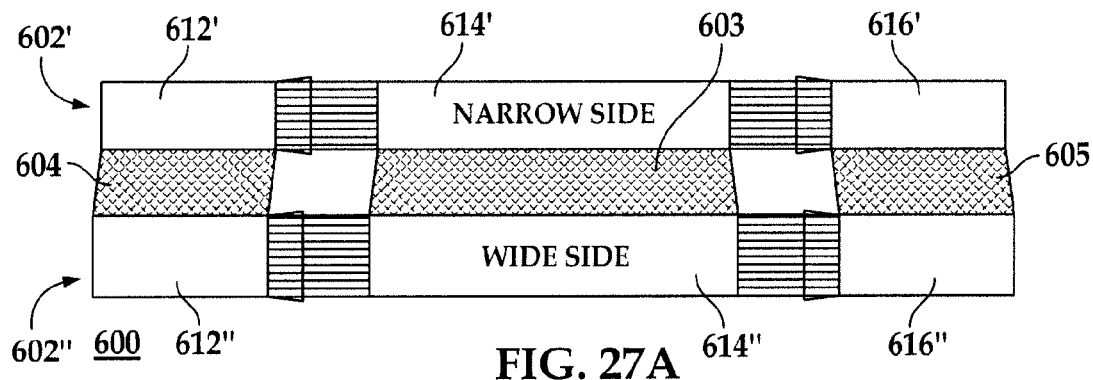
FIG. 27A illustrates an embodiment of a prosthetic device according to aspects of the present invention with a spacer knit panel.
Figure 27B:
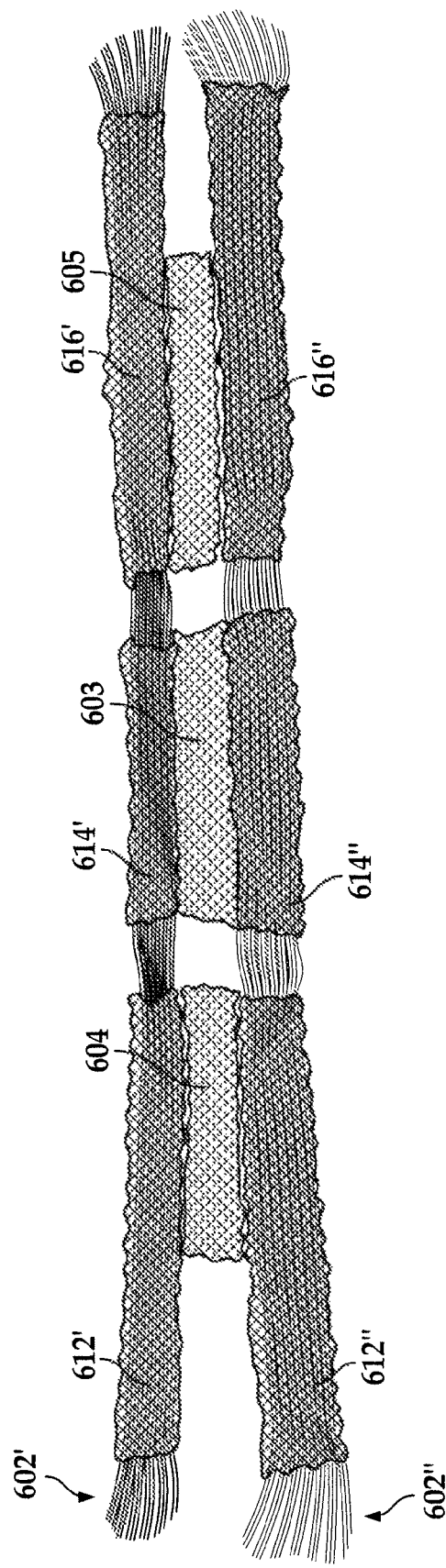
FIG. 27B illustrates the device of FIG. 27A.
Figure 27C:
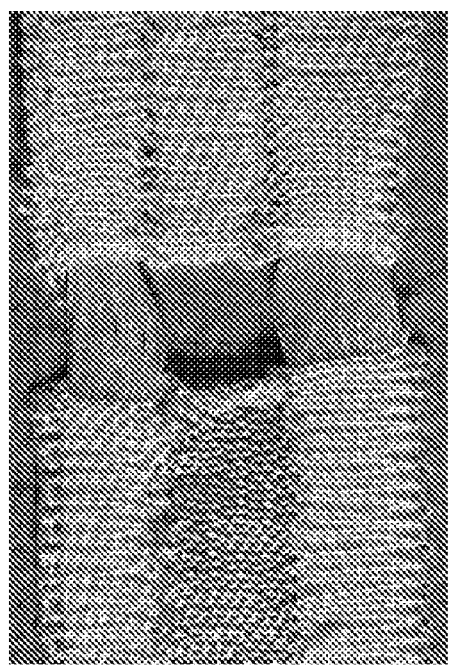
FIG. 27C illustrates a magnified section of FIG. 27B.

In alternative embodiments, the two bundles 602' and 602" may be joined by a knit between corresponding knitted section 612' and 612" and/or 616' and 616", as illustrated for example by connecting knit sections 604 and 605 in FIGS. 27A-B. Advantageously, the combination of connecting knit sections 603, 604, and 605 enable even bundle distribution when implemented in the bone tunnels. The connecting knit sections 603, 604, and 605 may be knitted in a manner similar to the knitted sections 612'/612", 614'/614", and 616'/616" with variations, such as different yarn size, different knit loop size, different loop interaxis, or any combination thereof, to achieve the desired distribution characteristics for the bundles.

In addition, FIG. 18A also illustrates protective tubular sections 640 positioned at an edge of the knitted sections 612'/612" and 616'/616" to minimize abrasion that occurs at these edges. The tubular sections 640 are similar to the tubular sections 340 described previously. In some embodiments, further abrasion protection may be achieved by extending the optional protective tubular sections 640 to the next adjacent knitting section and consequently covering the parallel intra-articular bundles 622'/622" and 624'/624". The tubular sections 640 may also be added to the femoral knitted sections 614'/614". In general, protective tubular sections are not limited to any particular knitted sections and may extend from any number and combination of the knitted sections.

Figure 19A:
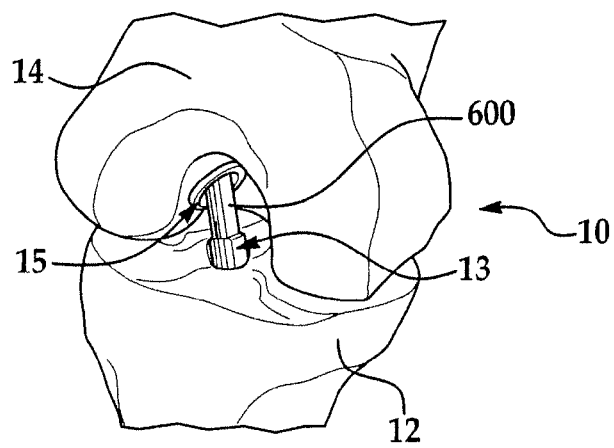
FIG. 19A illustrates the device of FIG. 18A anchored to a knee joint.

FIG. 19A illustrates the ligament prosthesis 600 extending between the tibial bone 12 and the femoral bone 14 in the knee 10. As further shown in FIG. 19B, the ligament prosthesis 600, when implemented in the knee 10, is folded longitudinally along an axis 601 and transversely across the knitted sections 614' and 614". As also illustrated in FIG. 18B, the knitted sections 612', 612", 616', and 616" form a tibial knit section 619 that fills a tibial bone tunnel 13. Meanwhile, the knitted sections 614' and 614" form a femoral knit section 620 that fills a femoral bone tunnel 15. Preferably, when implemented, the ends of the ligament prosthesis 600 do not require any cutting as the ligament prosthesis 600 remains in the bone tunnels. In some embodiments, the ends of the ligament prosthesis 600 may be cut following fixation or extra-osseous fixation may be employed outside the bone tunnel.

Figure 19B:
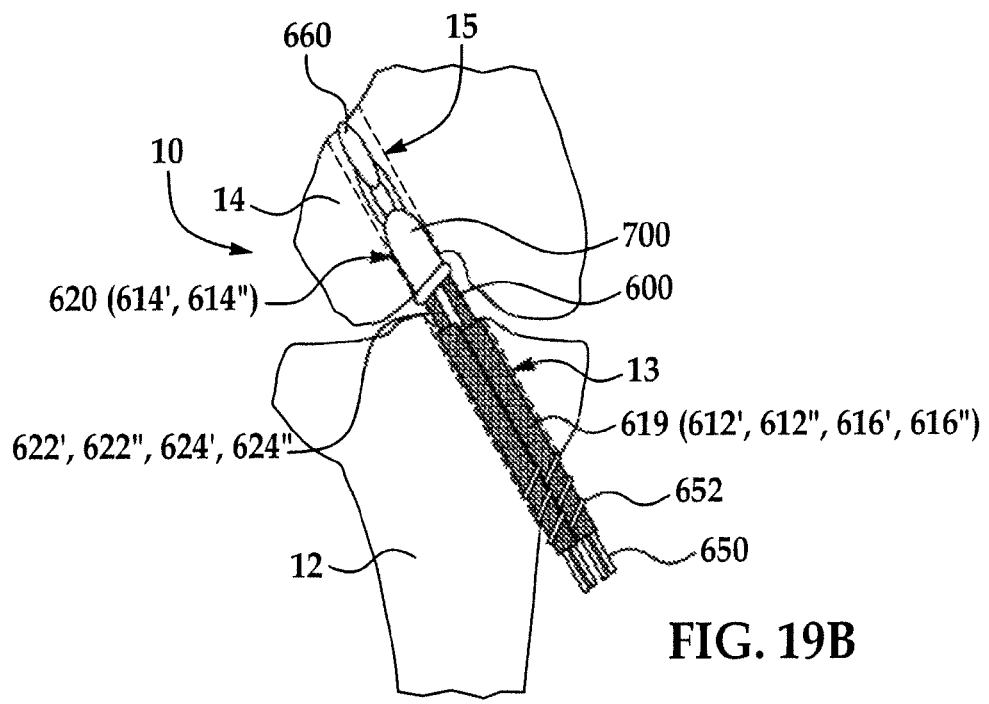
FIG. 19B further illustrates the device of FIG. 18A anchored to a knee joint.

As FIG. 19B shows, the femoral knit section 620 is disposed in a knitted sock device, or covering, 700, and the combination of the femoral knit section 620 and the sock device 700 fills the femoral bone tunnel 15. In addition, the sock device 700 includes a collar 720 that abuts the edge of the femoral bone tunnel 15. The sock device 700, which is described in further detail below, minimizes abrasion against the femoral bone tunnel aperture and may provide a press-fit at the aperture.

As illustrated in FIG. 19B, the intra-articular sections 622', 622", 624', and 624" combine to serve as a functional ligament. This combination of intra-articular sections 622', 622", 624', and 624" allows full functioning of the knee joint 10 while providing the necessary scaffolding and void volume for organized tissue in-growth and remodeling. Similar to the embodiments described previously, the intra-articular sections 622'/622" and 624'/624" are formed by one or more single continuous yarns 623'/623", i.e., weft bundles, connecting the knitted sections 612'/612", 614'/614", and 616'/616".

As FIG. 19B also illustrates, the tibial knit section 619 may be anchored to the knee 10 with suspensory fixation which where sutures 650 may extend longitudinally from the tibial knit section 619. As shown in FIGS. 18B and 19B, the sutures 650 may be used to create whip stitches 652 in each of the sections 612', 612", 616', and 616" forming the tibial knit section 619. These extensions of the sutures 650 may be used, for example, as a pretension linkage during anchoring of the device 600 and/or as an optional fixation mechanism. Meanwhile, the femoral knit section 620 may be anchored to the knee 10 via suspensory fixation device 660. The suspensory fixation device 660 may include a linkage that is operably connected to and anchors the femoral knit section 620. Anchoring may also be achieved through interference fixation in one or both of the tunnels and may not require the use of linkages or sutures.

As FIG. 30 illustrates, some embodiments of the prosthetic ligament 600 may also include a pocket 621 in the tibial section 619 that allows a screw to be inserted or a contained area to be filled with bone filler.

FIG. 18A shows loop-like knitted tubular structures 613 and 617 that extend longitudinally from the knitted sections 612'/612" and 616'/616", respectively. When the ligament prosthesis 600 is folded as shown in FIGS. 18B and 19B, the tubular structures 613 and 617 may accommodate the sutures 650 which can tension and/or anchor the tibial knit section 619 to the knee 10. In general, such tubular structures may be applied to any embodiments, including the other three-section and five-section prosthetic ligaments described above.

The knit structure of the tubular structures 613 and 617 may include the weft bundles formed by the single continuous yarns 623'/623". As such, the tubular structures 613 and 617 do not interfere with the weft bundles but actually provide a way to organize the weft bundles in parallel orientation. In addition, because the weft bundles extend through the tubular structures 613 and 617, a load applied to sutures 650 passing through the tubular structures 613 and 617 results in even tensioning and/or anchor load distribution of the weft bundles.

In an example technique, the tubular structures 613 and 617 may be formed by employing the following knitting sequence on a 16 gauge Shima Seiki SES122si flat bed knitting machine configured with Intarsia yarn guides as described above. Starting from left to right, Guide 2 lays the 18t yarn to form a series of loops on every other needle on the back needle bed within a predetermined section of the prosthetic ligament 600 that will include an tubular structure 613. After spanning the width of the tubular structure section 613, Guide 2 reverses and traverses right to left back across the tubular structure section 613, laying the 18t yarn to form a series of loops on the needles on the front needle bed opposing the previously loaded needles. After returning to the original starting point, the 18t yarn reverses and traverses left to right across the tubular structure section 613 laying the 18t yarn to form a series of loops on the remaining needles not loaded in the first pass. After spanning the width of the tubular structure section 613, Guide 2 reverses and transverses right to left, back across laying the 18t yarn forming a series of loops on the front needle bed opposing the needles loaded in the previous position on the back needle bed. The above sequence may be repeated one or more times to stabilize the bottom of the section 613. The same sequence is repeated for knitted section 617. In knitted sections 612'/612" and 616'/616", i.e., sections outside the tubular structures 613 and 617, the 18t yarn may secure the 36t yarn with interlock loops. In the tubular structure 613 and 617, the 18t yarn may form single jersey stitches to secure the 36t yarn.

Following the formation of the tubular structures 613 and 617 with the 18t yarn, the weft insertion yarn may be tucked in the knitted sections 612'/612" and 616'/616" in a manner similar to the sequence described for the ligament prosthesis 300. In the tubular structures 613 and 617, the weft insertion yarn may be tucked on the same needle bed as the yarn guide moves from left to right and may be tucked on the opposite needle bed as the yarn guide moves from right to left. Preferably, before a row of single jersey stitches with the 18t yarn is formed, no more than one 36t yarn is tucked and held by the same needle to prevent damage to the 36t yarn and to the needle.

Alternative techniques are contemplated for producing a prosthetic ligament with one or more tubular structures. For example, FIG. 26 illustrates a continuous loop graft 1000 that provides a tubular structure 1010. The tibial knit section 1011 is composed by a front section 1021 and a back section 1026. The intra-articular section 1012 is composed by a front section 1022 and a back section 1025. The femur section 1013 is composed by a front section 1023 and a back section 1024.

Figure 25A:
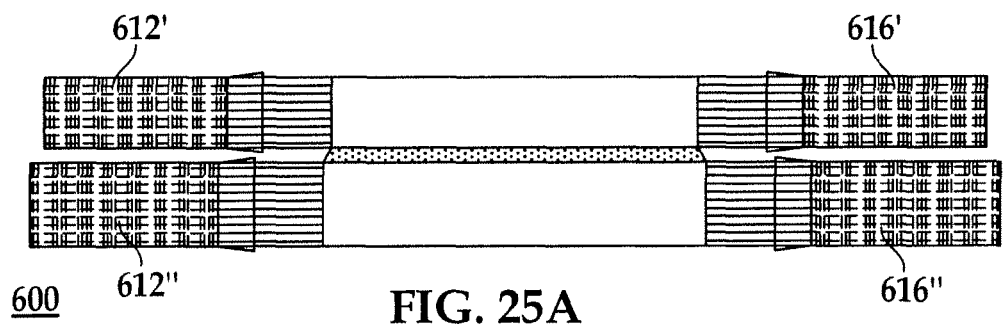
FIG. 25A illustrates an embodiment of a prosthetic device according to aspects of the present invention with a lower gauge knit.
Figure 25B:
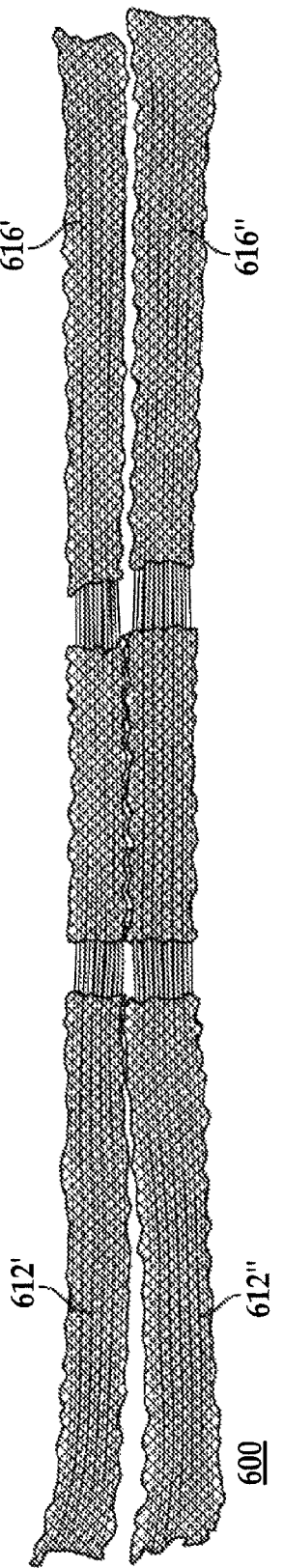
FIG. 25B illustrates the device of FIG. 25A.
Figure 25C:
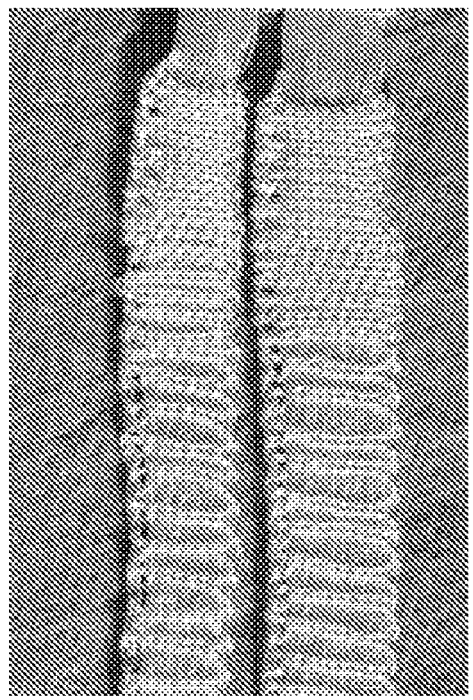
FIG. 25C illustrates a magnified section of FIG. 25B.

To facilitate alignment of the knitted sections 612', 612", 616', and 616" when the ligament prosthesis 600 is in the folded configuration, the knitted section 614' of the bundle 602' may have a shorter longitudinal length than the corresponding knitted section 614" of the other bundle 602". When the ligament prosthesis 600 is folded transversely at the knitted sections 614' and 614", the bundle 602" with the longer knitted section 614" may be folded over the bundle 602' with the shorter knitted section 614' to form an outer bundle of the ligament prosthesis 600. Due to the larger fold for the outer bundle 602" with the longer femoral sections 614", corresponding sections 612'/612" and 616'/616" of both bundles 602' and 602" are more easily aligned. Preferably, the inner bundle will be shortened by the radius of curvature of the ligament device when folded which is calculated as $1.5 \times \pi \times$ the graft thickness. The range of length differences between the two bundles of a ligament device may be from no difference to 30 mm, where larger differences may be desired to accommodate variations in anchor design. Additionally, the bundle 602' may be transversely narrower than the bundle 602", so that the bundle 602" can more easily form an outer bundle over the bundle 602' and better conform to the anchor and/or tunnel. Preferably, to create a balanced knit pattern, an odd number of weft insertion groups (where each insertion group may contain multiple yarns) may be included in each bundle of the device. In an example implementation, in a device with twenty-six weft insertion groups where each group contains four weft bundles/yarns, preferably, the wider device bundle will contain fifteen insertion groups and the narrower bundle eleven. In this example, it would be acceptable to have any combination of odd numbers that add to the total twenty-six insertions with a range from twenty-five insertions in the wider bundle and one insertion in the narrower bundle to thirteen insertions in both device bundles. FIGS. 25A-C illustrate an alternative embodiment of ligament prosthesis 600 with a half-gauge tunnel section in knit sections 612'/612" and 616'/616" to allow room for suturing and/or growth.

In an example implementation, the femoral knit section 620 formed by knitted sections 614' and 614" is pulled through the tibial bone tunnel 13 before being anchored in the femoral bone tunnel 15. As described previously, the femoral knit section 620 is disposed in a sock device 700 with a collar 720. To facilitate the movement of the femoral knit section 620 and the sock structure through the tibial bone tunnel 13, the tibial bone tunnel 13 may be larger than the femoral bone tunnel 15. For example, the tibial bone tunnel 13 may be approximately 8.5 mm in width or diameter, while the femoral bone tunnel 15 may be approximately 7.5 mm in width or diameter.

Figure 24A:
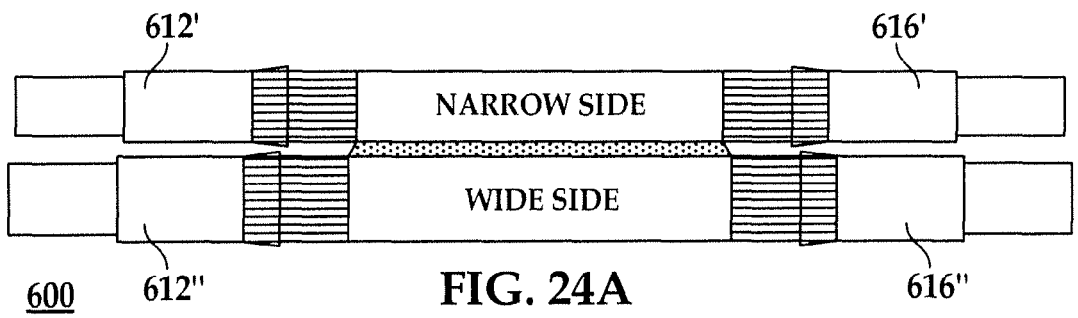
FIG. 24A illustrates an embodiment of a prosthetic device according to aspects of the present invention with varying device diameter within the knit sections.
Figure 24B:
FIG. 24B illustrates the device of FIG. 24A.
Figure 24C:
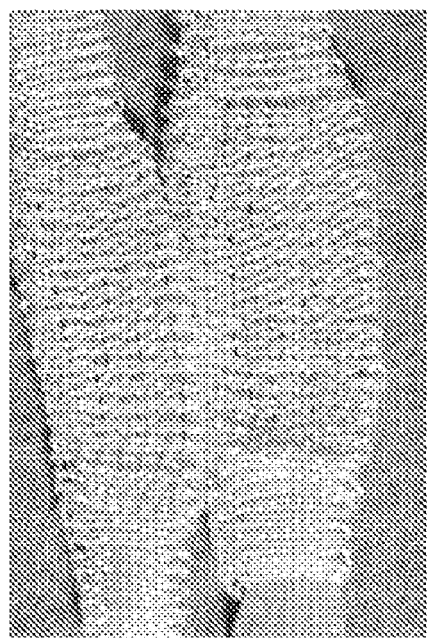
FIG. 24C illustrates a magnified section of FIG. 24B.

By using a larger yarn size for the knitted sections 612', 612", 616', and 616", a thicker tibial knit section 619 may be formed so that the fit of the tibial knit section 619 in the larger tibial bone tunnel 13 is comparable to the fit of the femoral knit section 620 in the smaller femoral bone tunnel 15. In other words, rather than having a gap between the tibial knit section 619 and the tibial bone tunnel 13, the tibial knit section 619 plugs the tibial bone tunnel 13 to achieve a press-fit and seal the tunnel 13. For example, the tibial knit section 619 may be formed with yarn ranging from 12t to 36t, while the femoral knit section 620 may be formed with 12t yarn to fit within a 8.5 mm tibial tunnel and a 7.5 mm femoral tunnel with 208 wefts. For other larger and smaller tunnel diameters in humans and/or canine stifles, the knit yarn within the smaller diameter may range from 5 μm to 2 mm and within the larger diameter may range from 5 μm to 2 mm as a function of tunnel diameter, desired void volume, and weft number and size. (In an alternative embodiment, the graft may be installed in the reverse direction, i.e., the tibial section may be pulled through the femoral bone tunnel 15 before being anchored in the tibial bone tunnel 13, in which case the femoral bone tunnel 15 may be larger than the tibial bone tunnel 13.) FIGS. 24A-C illustrate that an alternative embodiment of the prosthetic ligament 600 where the knit yarn diameter and/or the graft diameter at the knit sections 612'/612" and 616'/616" can be varied to plug the aperture of the bone tunnel while allowing space for an anchor.

Figure 33B:
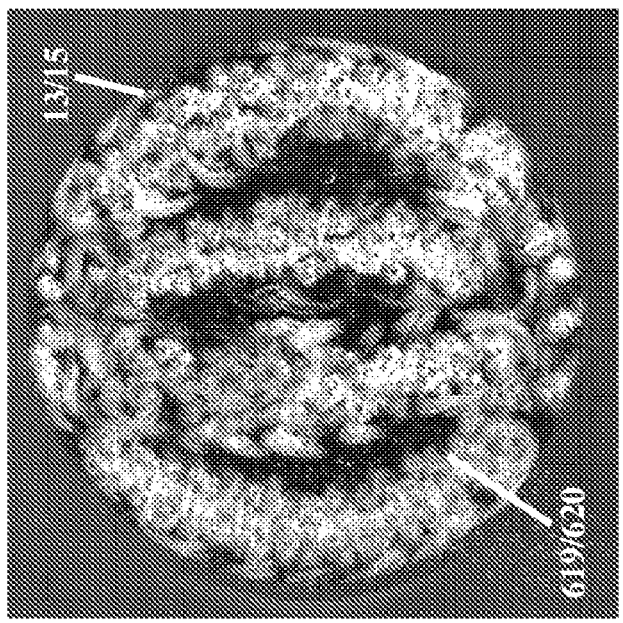
FIG. 33B illustrates a cross section of embodiment of a prosthetic device according to aspects of the present invention with a 5.0 mm loop length.
Figure 33A:
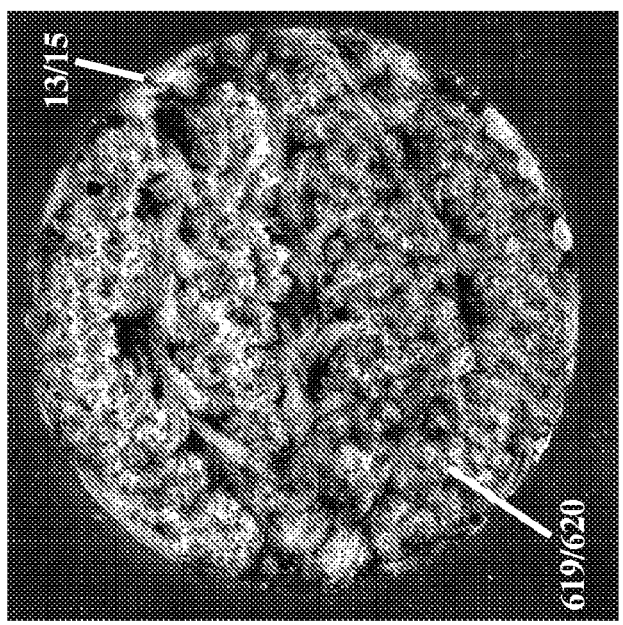
FIG. 33A illustrates a cross section of embodiment of a prosthetic device according to aspects of the present invention with a 5.5 mm loop length.

Alternatively, a desired fit between either knit section 619/620 and the bone tunnels 13/15 may be achieved by adjusting the length of the knitting loops in the knit sections 619/620. In particular, increasing the length of the loops provides a tighter fit while allowing the same yarn size, e.g., 12t yarn, to be used for both the tibial knit section 619 and the femoral knit section 320 when the tibial tunnel is a larger diameter than the femoral tunnel. In addition, employing longer loops may cause the knit sections 619/620 to conform to the shape of the bone tunnels 13/15 more easily. The loops lengths may be adjusted in increments as small as 10 μm. Table 8 contains the range of loop lengths that may be used. An example of the difference in conformity of a knit section 619/620 to a bone tunnel 13/15 is shown in FIGS. 33A and 33B, where two devices were knit with the same 24 filament yarns and the loop length varied from 5.5 mm to 5.0 mm. FIG. 33A illustrates a "loose" conformity, while FIG. 33B illustrates a "tight" conformity. Additionally, the loop length may be varied to modify conformity of ligament devices or other tissue support and replacement structures that do not require bone tunnels.

As another alternative, a desired fit between the tibial knit section 619 and the tibial bone tunnel 13 may be achieved by varying the inter-axis between two adjacent loops in combination with using a compensating knitting yarn size. For example, the same 16 gauge knitting machine may be employed in half gauge to produce a 8 gauge knit, while using a knitting yarn for the tibial section that is 1.5 or 2 times larger, for example, than the size of the yarn for the femoral section 620. Advantageously, this technique may provide a press fit and tunnel seal while allowing free area for bone ingrowth, anchor interface, and/or suture positioning.

Figure 26A:
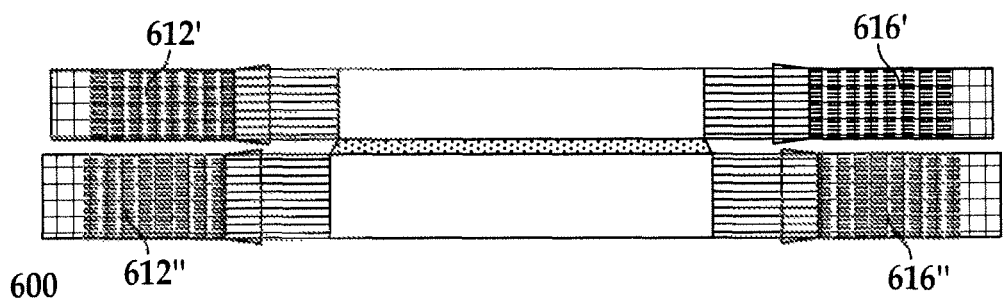
FIG. 26A illustrates an embodiment of a prosthetic device according to aspects of the present invention with a tapered knit.
Figure 26B:
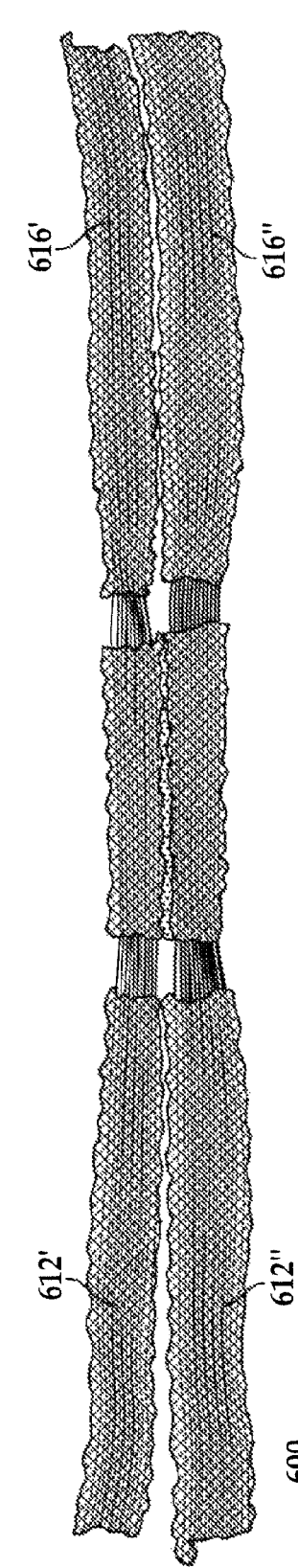
FIG. 26B illustrates the device of FIG. 26A.
Figure 28:
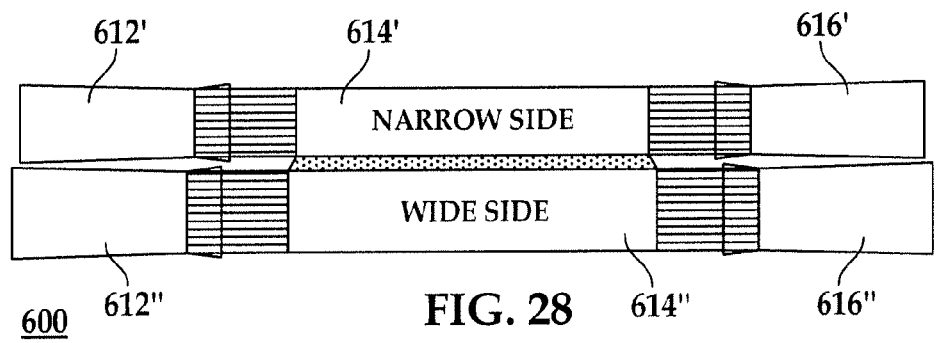
FIG. 28 illustrates an embodiment of a prosthetic device according to aspects of the present invention with flared knit ends.
Figure 26C:
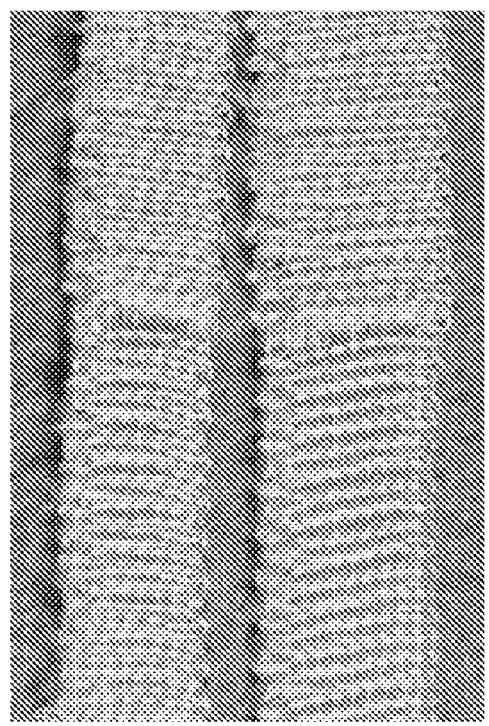
FIG. 26C illustrates a magnified section of FIG. 26B.
Figure 34:
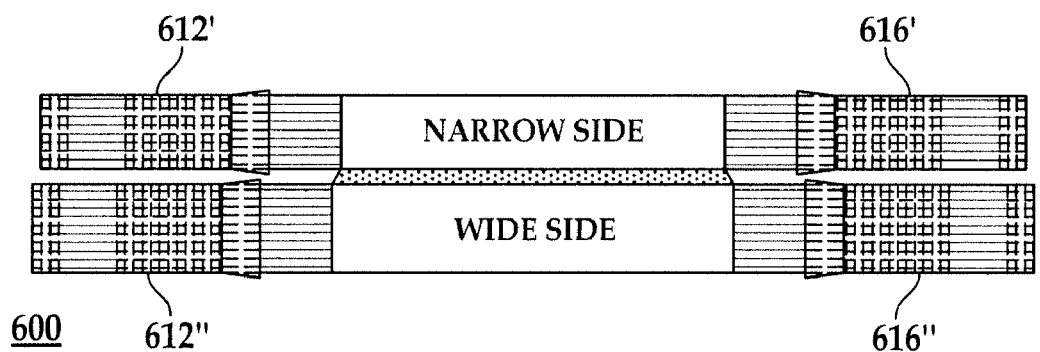
FIG. 34 illustrates an embodiment of a prosthetic device according to aspects of the present invention with an additional weft section within the knit.

FIGS. 26A-C illustrates an alternative embodiment of prosthetic ligament 600 with wefts extending further than others where the graft ends taper to a smaller distance for anchoring. FIG. 28 illustrates an alternative embodiment of prosthetic ligament 600 where the graft ends are flared to create a press-fit in a tapered bone tunnel. FIG. 34 illustrates an alternative embodiment of prosthetic ligament 600 where an additional weft section can be included within the knit sections for interface with anchors, such as a staple or post.

Figure 20A:
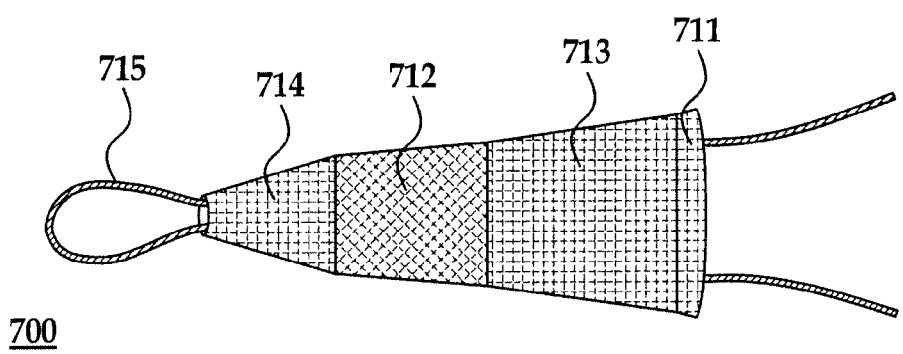
FIG. 20A illustrates a single knitted sock device that may be combined with a prosthetic device according to aspects of the present invention.
Figure 20B:
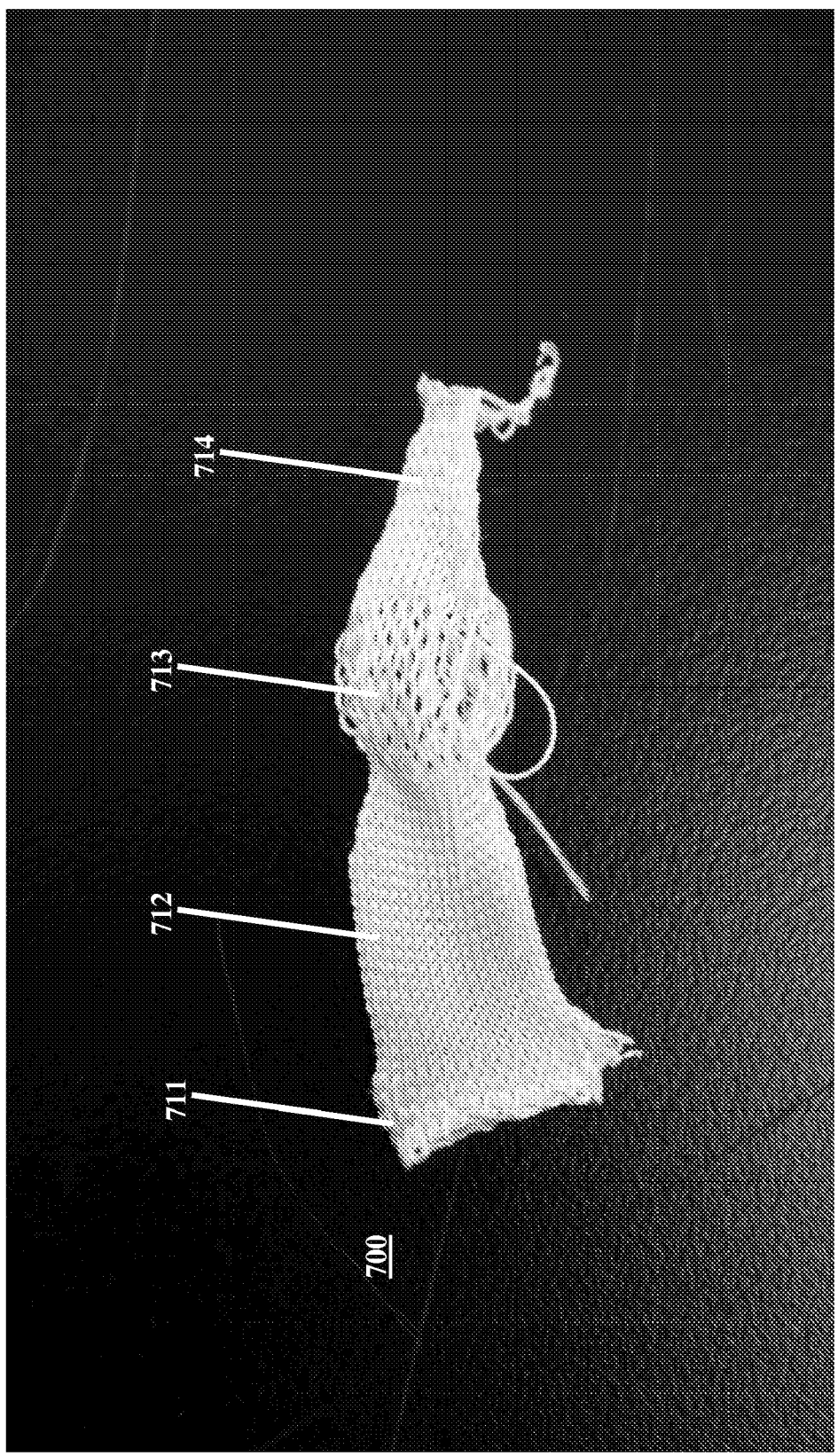
FIG. 20B illustrates the sock device of FIG. 20A.
Figure 20C:
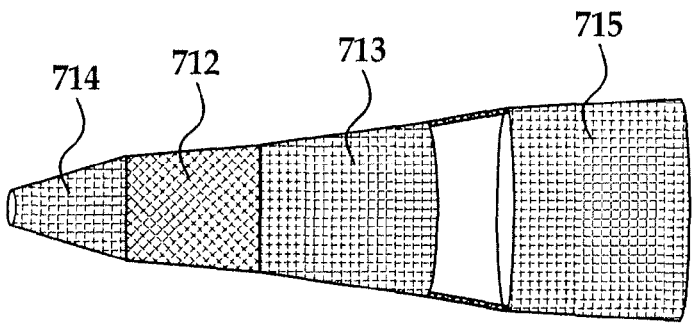
FIG. 20C illustrates another embodiment of a single knitted sock device that may be combined with a prosthetic device according to aspects of the present invention.
Figure 21:
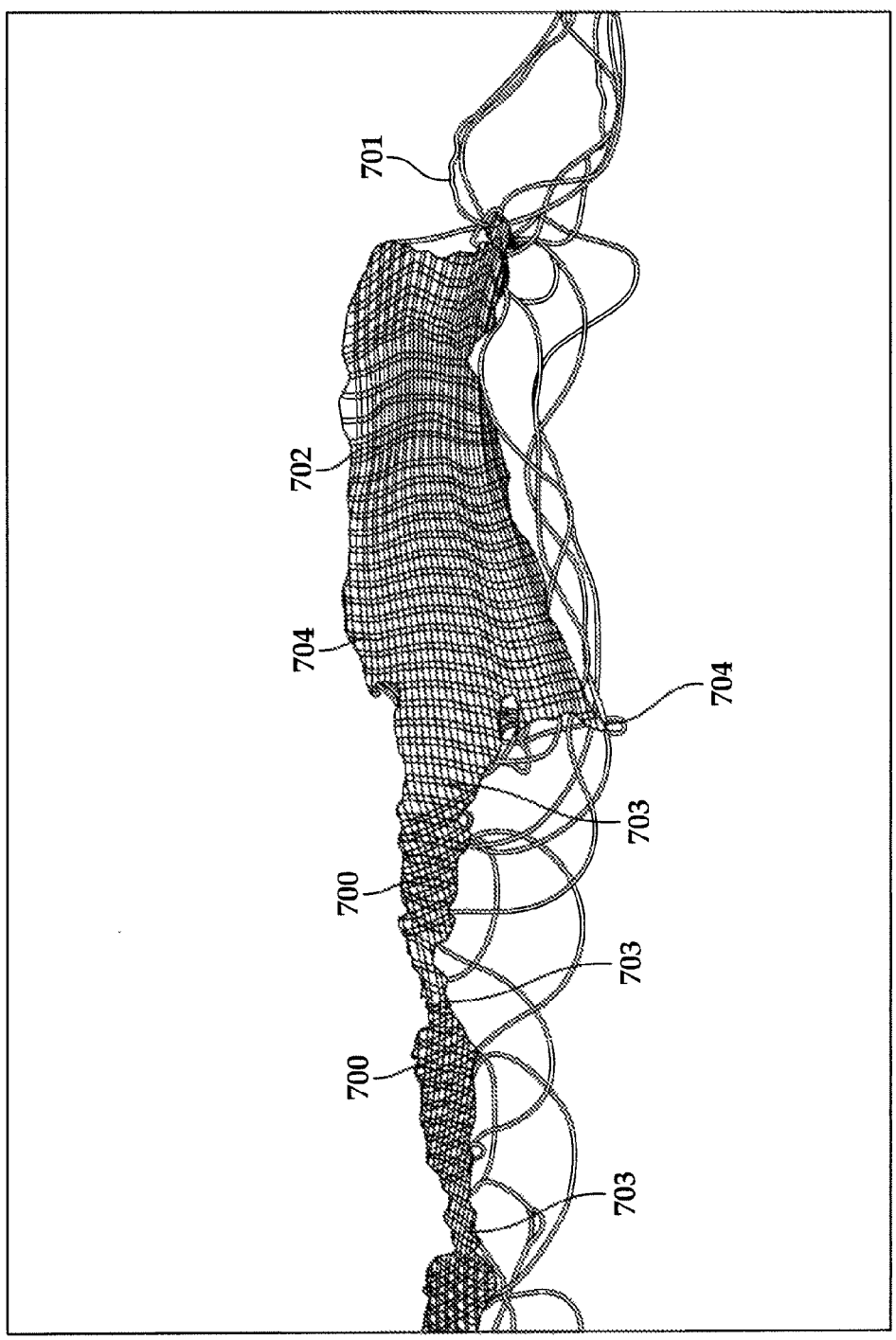
FIG. 21 illustrates a knitted sheet with a series of the sock devices of FIGS. 20A and B.

As described previously, the femoral knit section 620 is disposed in a sock device 700. FIGS. 20A and 20B further illustrate a knitted sock device 700 that can be combined with embodiments of the prosthetic ligaments described herein to minimize abrasion against the corresponding bone tunnel and/or to create a press-fit within the tunnel, such as the femoral bone tunnel 15. As shown in FIG. 20B, the sock device 700 includes four different sections: a section 711 made with 36t yarn, followed by a section 712 made with 18t yarn, followed by a section 713 made with 12t yarn, and followed by a section 714 made with 18t yarn. As shown in FIG. 20, the tubular knit design provides the sock device 700 with closed edges on all sides. In one example, the sock device 700 may be knitted on a 16 gauge Shima Seiki SES122si flat bed knitting machine configured with Intarsia yarn guides. The knitting machine is equipped with hold down sinker, pull down system, and yarn guides as described previously. FIG. 21 illustrates a series of sock device units 700 that may be produced on such equipment. However, it is contemplated that the sock device 700 may also be knit on a number of the other systems, including, but not limited to, those previously described.

In one example, initially, referring to the guide number on the machine, Guide 8 of the machine is set up with SSUPY yarn (Shima Start Up Yarn) 701, as shown in FIG. 21. The SSUPY yarn 701 spans a number of needles corresponding to the desired width of the product in addition to 10 or more needles per side, preferably 12 needles per side. These additional needles provide the correct comb tension throughout the start-up process. Guide 7 is set up with start-up, or waste, yarn 702 which provides sufficient knitted fabric for the main roller system to engage and to hold the product in tension as it is knitted, without damaging the actual knitted product. Guide 2 is set up with 12t yarn, which is delivered to knit, from left to right, the knitted section 713 of the sock device 700. Guide 3 is set up with 18t yarn, which is delivered to knit, from left to right, the knitted sections 712 and 714 of the sock device 700. Guide 5 is set up with 36t yarn, which is delivered to knit, from left to right, the knitted section 711 of the sock device 700. Guide 6 is set up with 15t yarn, which is delivered to knit, from left to right the separation section 703 shown in FIG. 21. The separation section 703 provides a "draw thread" yarn, which is looped in between the waste yarn and the first tubular device unit, and in between successive units. Accordingly, pulling the draw thread separates each unit from the others.

TABLE 9 provides the details of the Intarsia yarn guide, in order from front to back as they are set up on the flat bed knitting machine. The yarn supplied to each Intarsia guide is measured out by a digitally controlled stitch cam. The length of the knit loops is adjustable to 10 μm and the cam continually adjusts the yarn unwind so that the length of each knit loop in every row remains consistent throughout the entire product.

TABLE 9

| Guide 2 | Guide 3 | Guide 5 | Guide 6 | Guide 7 | Guide 8 |
|---|---|---|---|---|---|
| 12t for Section 713 | 18t for Sections 712 and 714 | 36t for Section 711 | "Draw Thread" | Waste Yarn | SSUPY |

After the SSUPY yarn 701 is hooked on the appropriate needles and grabbed by the comb, waste fabric is knitted in tubular single jersey knits from the waste yarn 702 across several rows. Towards the end of the waste fabric, the additional needles necessary to provide the correct comb tension are cast off 704. Two courses of tubular single jersey knits are made with the waste yarn 702, followed by two more courses with the "draw-thread" yarn 703. Next, the Guide 5 lays the 36t yarn to form a series of loops on every other needle across section 711 on the back needle bed. Then, the 36t yarn reverses and traverses right to left back across the section 711, laying the 36t yarn to form a series of loops on the needles on the front needle bed opposite to the previously loaded needles. After returning to the original starting point, the 36t yarn reverses and traverses left to right across section 711 laying the 36t yarn to form a series of loops on the remaining needles not loaded in the first pass. Then, the 36t yarn reverses and traverses right to left, back across section 711 laying the 36t yarn forming a series of loops on the front needle bed opposing the needles loaded in the previous position on the back needle bed. The sequence may be repeated one or more times to stabilize the bottom of section 711. Next, two course of single jerseys on the front and back needle bed are formed with the 36t yarn to complete section 711. Following this, a total of 31 courses of front and back needle bed single jersey are formed by the 18t yarn. Then, the furthest right needle of the front needle bed transfers to the second needle from the right on the back needle bed while the furthest right needle of the back needle bed transfers to the second needle from the right on the front needle bed. The resulting tubular knit fabric is now one needle narrower per needle bed than at start up resulting in a structure that follows the contour of the prosthetic ligament. This shaping procedure is repeated for a total of three times alternating between right side and left side and separated by one to three courses of single jersey on the front and back needle bed. The shaping procedures alternate from the left side, to the right side in sequence. For example, the furthest front right loop will transfer to the second left back needle and the furthest back left loop will transfer to the second front loop. After completion of ten courses single jersey, in the front and back needle bed, with the 12t yarn, eight more shaping steps as described above occur with the 18t yarn reducing the width of the tubular fabric to four needles on the front needle bed and four needles on the back needle bed. The final needle quantity is chosen based on the flat bed knitting machine gauge to allow the passage of a preferred fixation device through the end of the tubular section 714.

The formation of the sock device 700 concludes with a "bind-off" row for the front and back tubular structure. An exemplary bind-off technique starts from the farthest left in section 714, racks the back needle bed one needle position to the right, and transfers the first left loop of the front needle bed to one needle position to the left on the back bed. A new knit loop is then laid onto the first loop on the back needle bed and is subsequently transferred to the corresponding empty needle on the front bed. The back bed is then racked one needle position to the left and the first knit loop on the front needle is transferred to the back bed one needle to the right. The sequence is repeated across until the end of the section 714.

The bind off procedure direction is reversed to bind off all the remaining loops on the back needle bed as the draw thread is inserted. A knit loop is transferred from the back needle bed to the opposite needle on the front bed. A new knit loop is then laid onto the vacated needle on the back bed with the 15t draw thread. The back bed is then racked and the knit loop on the front needle is transferred to the back bed one needle to the left. The sequence is repeated across until only one loop remains and the sock device 700 is successfully closed off with a finished edge and can be simply detached from the other units with the draw-thread.

The teachings provided for the pattern for the sock device 700 can be applied to fit the range of dimensions, for example, indicated in TABLE 8 for the Length of $2^{nd}$ Knitted Section corresponding to the femur section length of the ligament prosthesis as well as a range of diameters of the ligament device. Additionally, the number of regions forming the sock device 700 may vary in number from the four sections 711, 712, 713, and 714 described previously, for example to a single section. The sock device 700 may or may not have an opening for suspensory fixation. To knit the sock device 700, yarn diameters ranging from approximately 5 µm to 2 mm may be used as a function of the bone tunnel and graft diameters.

The loop size used in knitting sections 711, 712, 713 and 714 may be varied according to the function of each section. To achieve increased abrasion resistance and increased fabric rigidity, a smaller loop size may be employed. On the other hand, a larger loop size may be employed to achieve increased elasticity and increased porosity. For example, a larger loop size in section 713 allows the sock device 700 to stretch more easily, particularly when it is being handled for anchoring. For example, when using an Endo-Button® to anchor the prosthetic ligament 300 described above, the fixation device must be toggled as it exits the femoral tunnel 15 and section 711 is secured at the entrance of the femoral tunnel 15. This technique provides a means to allow the sock to pass through the tunnels and to strength to allow the anchor to be seated while maintaining structural and dimensional integrity of the sock. In addition, the knit pattern can be maintained to allow bone ingrowth. The loop size in section 713 is larger than section 711, because a lower filament yarn is used and abrasion resistance must be higher in this area. Meanwhile, the loop size in section 714 is higher than section 713, because it is necessary to increase rigidity in order to prevent the ligament prosthesis from breaching the sock device 700 as the combination passes through the tunnels 13 and 15.

Alternatively, the ligament prosthesis 600 may be folded longitudinally, passed through a suspensory fixation device 660 and folded transversely at knitted sections 614' and 614" over the fixation device 660, as described above. The thread leader 662 that has previously been threaded through the suspensory fixation device 660 may be fed into the closed end of the lasso-like yarn 715 (as shown in FIG. 20A) in the sock structure 700. The free ends of the lasso-like yarn 715 may be pulled out of the sock structure 700 to place the thread leader 662 through the sock structure 700. The lasso-like yarn 715 may then be discarded. The sock structure 700 may than be moved over the femoral knit section 620 of the ligament prosthesis until it is completely seated on the femoral section. Before implantation, a suture may be passed through and knotted to the sock structure 700 as well as the femoral knit section 620 to ensure the correct alignment during handling.

Figure 22:
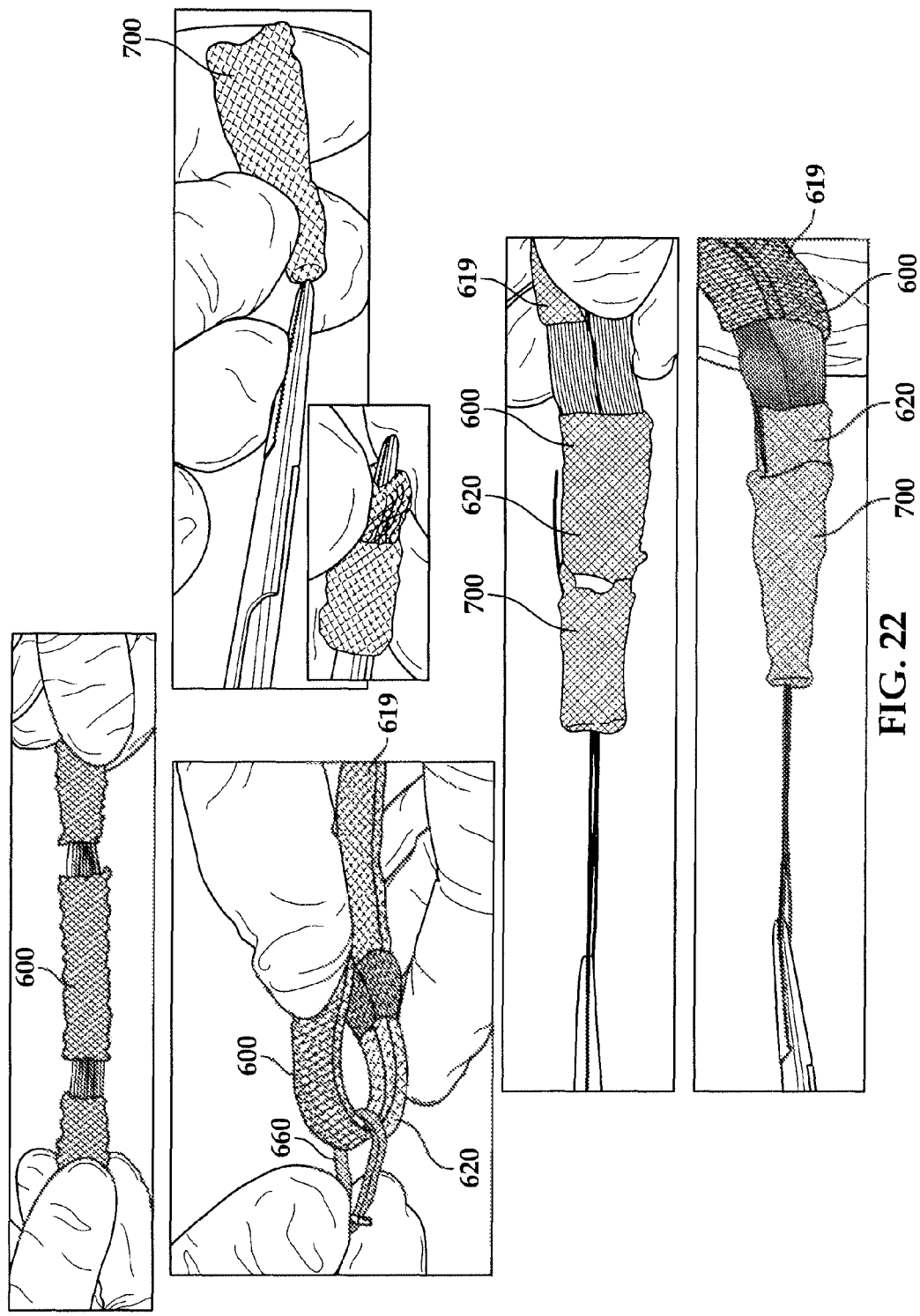
FIG. 22 illustrates an exemplary technique for assembling the sock device on the prosthetic device.
Figure 23:
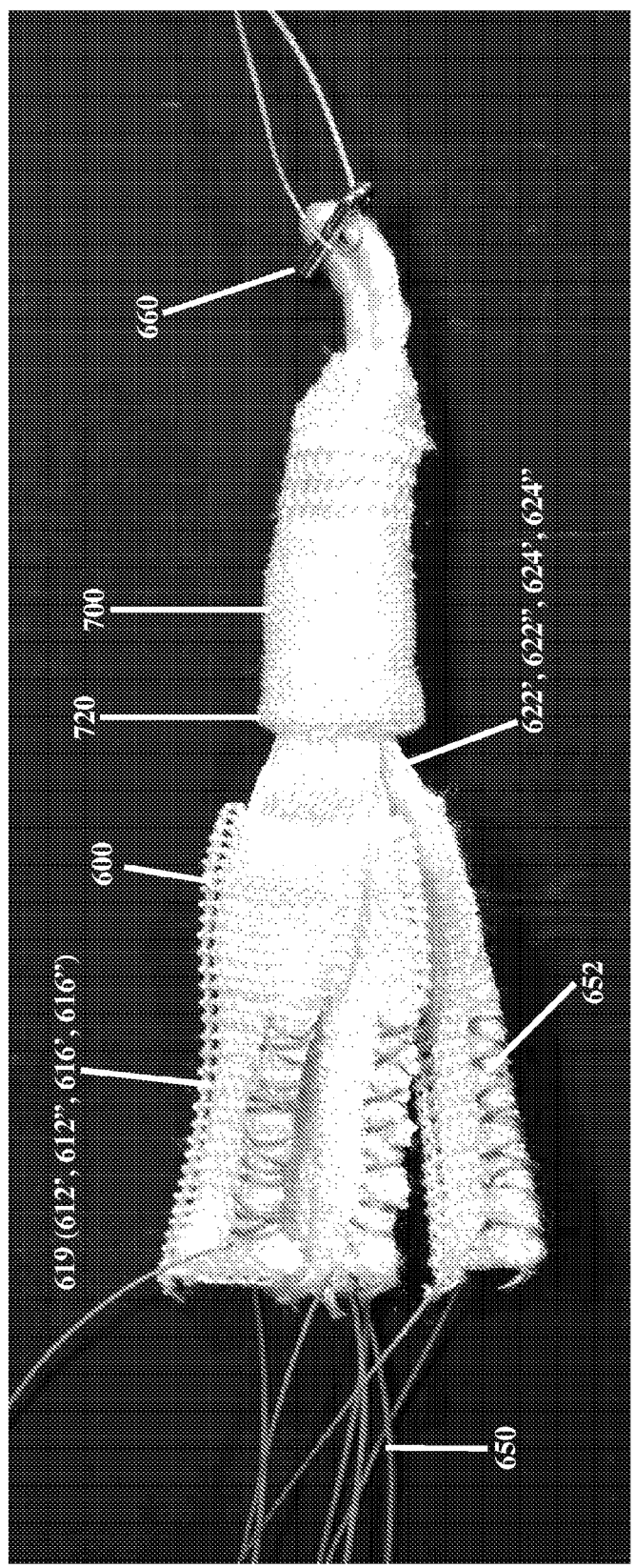
FIG. 23 illustrates an assembled embodiment of a prosthetic device according to aspects of the present invention.

Accordingly, FIG. 22 illustrates the ligament prosthesis 600 in combination with the sock device 700. In sum, the assembly shown in FIG. 22 includes the tibial knit section 619 which is installed in the tibial bone tunnel 13 with the sutures 650. In addition, this assembly includes the femoral knit section which is disposed in the sock device 700 and which is installed in the femoral bone tunnel 15 with the suspensory fixation device 660. The femoral knit section anchor and the whip stitching 652 on the tibial knit section 619 provide a technique for pretensioning prior to anchoring. As previously described, the ligament design may be compatible with any commercially available anchor for ACL fixation. It is also understood that embodiments according to aspects of the present invention may be installed in an over-the-top position without need for a femoral bone tunnel for example.

Furthermore the different variations described demonstrate the ability to tailor the fabric construction by varying the tibial knit density, shape and size for current and possibly future anchor design. For example tapering the anchor end of the tibia will allow a press fit anchor, while extending all of the weft insertion or part of the weft insertion beyond the end of the tibia will provide distribution of the load to each bundle.

It is contemplated that the sock device 700 may include additional features. For example, FIG. 20C illustrates an embodiment of the sock device 700 with the addition of an elongated tubular structure 770 attached at the end of the widest section of the sock device 700. The elongated tubular structure 770 will extend to cover the intra-articular section of the ligament prosthesis to offer protection of the area from abrasion. In another embodiment the elongated tubular structure 770 will extend beyond the intrarticular section passed the tibia section of the ligament prosthesis to prevent abrasion in the intrarticular section as well as the tibia section.

In addition, FIG. 31 illustrates alternative applications of a sock device 1100. In order to prevent abrasion against the tibia bone, the sock device 1100 is positioned around the tibial knit section 619. The sock device 1100 also may also determine the distribution of the bundles in the tunnel according to loop size and or yarn size. Similarly, FIG. 32 illustrates a different application of a sock device 1200, where the sock device 1100 has the shape of a tubular single sleeve that is installed over the femur graft 1111 prior to folding.

Although some embodiments described herein may be specifically applied as prosthetic ligaments for reconstructing an ACL, it is understood that embodiments according to aspects of the present invention are not limited to such applications. Embodiments may be employed for all soft tissue support and replacement, including, but not limited to, ligaments and tendons of the knee, stifle, ankle, foot, elbow, shoulder, wrist, hand and spine, bladder and urethra slings, neck and face lift support, body wall repair, restore pelvic floor, hernia repair, paravaginal repairs, reinforcement and buttressing of staple lines, closure of an abdominal incision, repair of anorectal fistulas, dural substitute for repairing dura mater, and organ repair or suspension.

Figure 29:
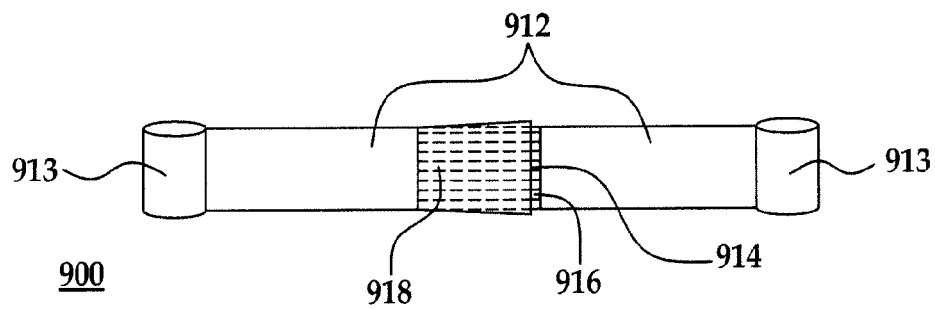
FIG. 29 illustrates an embodiment of a prosthetic device according to aspects of the present invention with an extended tubular cuff.

Additionally, the prosthetic devices may be used in humans, primates and/or any quadrupeds including canines. For example, FIG. 29 illustrates an embodiment of a canine prosthetic ligament 910 that may be employed for over-the-top reconstructions of a canine ACL. In particular, the prosthetic ligament 910 has two intra-osseous knitted sections 912 and an intra-articular knitted section 914, which includes one or more single continuous weft insertion yarns 916 extending between the two intra-osseous knitted sections 912. The canine prosthetic ligament 910 also includes knitted anchor sections 913. As shown in FIG. 29, the canine prosthetic ligament 910 employs a protective tubular sections 918 that extends from one intra-osseous knitted section 912 to the other, thereby covering the intra-articular knitted section 914. The tubular sections 918 minimizes abrasion that may occur on areas of bone that contact the canine prosthetic ligament 910. In an over-the-top implementation, the intra-osseous knitted section 912 would otherwise cause such abrasion.

While the present invention has been described in connection with a number of exemplary embodiments, and implementations, the present inventions are not so limited, but rather cover various modifications, and equivalent arrangements, which fall within the purview of prospective claims. All dimensions, measurements, and the like, provided herein are exemplary.

What is claimed is:

1. A prosthetic device comprising:
   at least two knitted sections, each knitted section including at least one row of fiber; and
   at least one section disposed between the at least two knitted sections, the at least one section disposed between the at least two knitted sections comprising at least one single continuous fiber traversing the at least one section disposed between the at least two knitted sections and the at least two knitted sections, the at least one single continuous fiber forming a plurality of traverses extending between the at least two knitted sections,
   wherein the at least two knitted sections and the at least one single continuous fiber comprise sericin extracted silk fibroin fibers in a form of a yarn and
   wherein the sericin extracted silk fibroin fibers are substantially non-antigenic.

2. The device according to claim 1, wherein the plurality of traverses extending between the at least two knitted sections are substantially parallel.

3. The device according to claim 1, wherein the at least one single continuous fiber is received into the at least one row of each knitted section.

4. The device according to claim 1, wherein the at least one single continuous fiber is tucked in the at least one row of each knitted section.

5. The device according to claim 1, wherein the at least one single continuous fiber is tucked to at least one loop in each knitted section.

6. The device according to claim 5, wherein the at least one loop is formed by the at least one single continuous fiber.

7. The device according to claim 5, wherein the at least one loop is formed in each knitted section.

8. The device according to claim 1, wherein the at least one row of the at least two knitted sections comprises a plurality of rows, and the at least one single continuous fiber traverses, at least once, each of the plurality of rows.

9. The device according to claim 8, wherein the at least one single continuous fiber is received into the plurality of rows.

10. The device according to claim 9, wherein the at least one single continuous fiber is received more than once into each of the plurality of rows.

11. The device according to claim 1, wherein the at least one single continuous fiber traverses more than once between the at least two knitted sections by pivoting in at least one of the knitted sections.

12. The device according to claim 11, wherein the at least one single continuous fiber pivots past a first edge of the at least one of the knitted sections, the first edge being adjacent to the section disposed between the at least two knitted sections.

13. The device according to claim 11, wherein the at least one single continuous fiber pivots at a second edge of the at least one of the knitted sections, the second edge opposing a first edge adjacent to the section disposed between the at least two knitted sections.

14. The device according to claim 11, wherein the at least one single continuous fiber pivots beyond a second edge of the at least one of the knitted sections, the second edge opposing a first edge adjacent to the section disposed between the at least two knitted sections.

15. The device according to claim 11, wherein the at least one single continuous fiber pivots more than once within the at least one row of at least one of the knitted sections.

16. The device according to claim 1, wherein the at least one single continuous fiber is received more than once into the at least one row of at least one of the knitted sections.

17. The device according to claim 1, further comprising a protective tubular section positioned at an edge of each of the knitted sections.

18. The device according to claim 1, wherein the at least two knitted sections and the at least one single continuous fiber are bioresorbable.

19. The device according to claim 1, wherein the at least two knitted sections and the at least one single continuous fiber have a surface treatment.

20. The device according to claim 1, wherein the at least one row of each knitted section comprises multiple rows, the at least one single continuous fiber comprises a plurality of single continuous fibers, and the at least one section disposed between the at least two knitted sections is comprised of the plurality of single continuous fibers and connects the multiple rows of the knitted sections.

21. The device according to claim 1, wherein the at least two knitted sections are comprised of a weft knitted section.

22. The device according to claim 1, wherein the at least two knitted section are comprised of a warp knitted section.

23. The device according to claim 1, wherein the at least one single continuous fiber is received in and traverses the at least two knitted sections in a repetitive pattern moving from a first of the knitted sections, through the at least one section disposed between the at least two knitted sections, through a second of the knitted sections, and back through the at least one section disposed between the at least two knitted sections and the first of the knitted sections.

24. The device according to claim 23, wherein the repetitive patter is a S pattern.

25. The device according to claim 23, wherein the repetitive pattern is a Z pattern.

26. The device according to claim 23, wherein one or more of the traverses of the at least one continuous fiber is received into a single row of the at least two knitted sections to form a plurality of the traverses before transitioning to a next row of the at least two knitted sections.

27. The device according to claim 1, wherein the at least two knitted sections comprise at least three knitted sections, a section being disposed between pairs of the knitted sections, and the knitted sections and the sections disposed between the at least two knitted sections being formed of the at least one single continuous fiber.

28. The device according to claim 1, wherein edges of each knitted section are finished to prevent unraveling.

29. The device according to claim 28, wherein the finished edges are substantially parallel to the at least one single continuous fiber and are finished with a closed bind-off.

30. The device according to claim 1, further comprising a separating section extending along an upper edge of the at least two knitted sections and the at least one section disposed between the at least two knitted sections.

31. The device according to claim 1, wherein the at least two knitted sections comprise a combination of atlas and closed tricot knitting patterns.

32. The device according to claim 1, further comprising at least one knitted tubular structure extending from one of the knitted sections, wherein the at least one single continuous fiber passing through the tubular structure and receiving a load applied to the tubular structure.

33. The device according to claim 1, wherein the at least two knitted sections have different knit structures.

34. The device according to claim 33, wherein the different knit structures vary according to at least one of knit loop size and yarn size.

35. A prosthetic device comprising:
a plurality of knitted sections; and
a section disposed between two consecutive knitted sections, the knitted sections and the sections disposed between two consecutive knitted sections being comprised of at least one single continuous fiber, the at least one single continuous fiber forming a plurality of traverses extending between at least two knitted sections, and
wherein the two knitted sections and the at least one single continuous fiber comprise sericin extracted silk fibroin fibers in a form of a yarn and
wherein the sericin extracted silk fibroin fibers are substantially non-antigenic.

36. The device according to claim 35, wherein the plurality of traverses extending between the plurality of knitted sections are substantially parallel.

37. The device according to claim 35, wherein the at least one single continuous fiber is received into at least one row of each of the plurality of knitted sections.

38. The device according to claim 35, wherein the at least one single continuous fiber is tucked into at least one row of each of the plurality knitted sections.

39. The device according to claim 35, wherein the at least one single continuous fiber is tucked to at least one loop in each of the plurality of knitted sections.

40. The device according to claim 39, wherein the at least one loop is formed by the at least one single continuous fiber.

41. The device according to claim 39, wherein the at least one loop is formed in each of the plurality of knitted sections.

42. The device according to claim 35, wherein the at least one row of the plurality of knitted sections comprises a plurality of rows, and the at least one single continuous fiber traverses, at least once, each of the plurality of rows.

43. The device according to claim 42, wherein the at least one single continuous fiber is received in to the plurality of rows.

44. The device according to claim 43, wherein the at least one single continuous fiber is received more than once into each of the plurality of rows.

45. The device according to claim 35, wherein the plurality of knitted sections and the at least one single continuous fiber are bioresorbable.

46. The device according to claim 35, wherein the plurality of knitted sections and the at least one single continuous fiber have a surface treatment.

47. The device according to claim 35, wherein the at least one row of each of the plurality of knitted sections comprises multiple rows, the at least one single continuous fiber comprises a plurality of single continuous fibers, and the at least one section disposed between two consecutive knitted sections is comprised of the plurality of single continuous fibers connecting the multiple rows of the knitted sections.

48. The device according to claim 47, wherein the plurality of knitted sections are comprised of a weft knitted section.

49. The device according to claim 47, wherein the plurality of knitted sections are comprised of a warp knitted section.

50. The device according to claim 47, wherein the at least one single continuous fiber is received in and traversed in a repetitive pattern moving from a first of the knitted sections, through the at least one section disposed between two consecutive knitted sections, through a second of the knitted sections, and back through the at least one section disposed between two consecutive knitted sections and the first of the knitted sections.

51. The device according to claim 50, wherein the repetitive pattern is a S pattern.

52. The device according to claim 50, wherein the repetitive pattern is a Z pattern.

53. The device according to claim 50, wherein one or more of the traverses of the at least one continuous fiber is received into a single row of the plurality of knitted sections to form a plurality of the traverses before transitioning to a next row of the at least two knitted sections.

54. The device according to claim 35, wherein the plurality of knitted sections comprises at least three knitted sections, an section being disposed between pairs of the knitted sections, and the knitted sections and the sections disposed between two consecutive knitted sections including the at least one single continuous fiber.

55. The device according to claim 35, wherein edges of each of the plurality of knitted sections are finished to prevent unraveling.

56. The device according to claim 55, wherein the finished edges are substantially parallel to the at least one single continuous fiber and are finished with a closed bind-off.

57. The device according to claim 35, further comprising a separating section extending along an upper edge of the plurality of knitted sections and the at least one intermediate section.

58. The device according to claim 35, wherein the plurality of knitted sections comprise a combination of atlas and closed tricot knitting patterns.

59. A prosthetic device comprising:
a component having a component surface; and
a knitted covering positioned over the component surface, the knitted covering providing an exterior surface that is less abrasive than the component surface,
wherein the knitted covering comprises sericin extracted silk fibroin fibers in a form of a yarn and
wherein the sericin extracted silk fibroin fibers are substantially non-antigenic.

60. The device of claim 59, wherein the knitted covering has an interior and a portion of the component is disposed within the interior.

61. The device of claim 59, wherein the covering has a plurality of knitted sections having different knit structures.

62. The device of claim 59, wherein the different knit structures vary according to at least one of knit loop size and yarn size.

63. The prosthetic device of claim 1, wherein the silk fibroin fibers are *Bombyx mori* silkworm silk fibroin fibers.

64. The prosthetic device of claim 1, wherein the sericin extracted silk fibroin fibers contain substantially no sensitizing agents.

65. The prosthetic device of claim 1, wherein the at least two knitted sections and the at least one section disposed between the at least two knitted sections have a yarn size that does not vary in the device.

66. The prosthetic device of claim 1, wherein the at least two knitted sections and the at least one section disposed between the at least two knitted sections have a yarn size that does not vary within a section of the device.

67. A support structure for soft tissue support and replacement comprising:
at least two knitted sections, each knitted section including at least one row of fiber; and
at least one section disposed between the at least two knitted sections, the at least one section disposed between the at least two knitted sections comprising at least one single continuous fiber traversing the at least one section disposed between the at least two knitted sections and the at least two knitted sections, the at least one single continuous fiber forming a plurality of traverses extending between the at least two knitted sections, wherein the at least two knitted sections and the at least one single continuous fiber comprise sericin extracted silk fibroin fibers in a form of a yarn and wherein the sericin extracted silk fibroin fibers are substantially non-antigenic.

68. The support structure of claim 67, wherein the silk fibroin fibers are *Bombyx mori* silkworm silk fibroin fibers.

69. The support structure of claim 67, wherein the sericin extracted silk fibroin fibers contain substantially no sensitizing agents.

70. The prosthetic device of claim 1, wherein the at least two knitted sections and the at least one section disposed between the at least two knitted sections have a yarn size that does not vary in the device.

71. The prosthetic device of claim 1, wherein the at least two knitted sections and the at least one section disposed between the at least two knitted sections have a yarn size that does not vary within a section of the device.

72. A prosthetic device comprising:
at least one knitted section; and
at least one single continuous fiber traversing the at least one knitted section, the at least one single continuous fiber forming a plurality of traverses extending through the at least one knitted section, and
wherein the at least one knitted section and the at least one single continuous fiber comprise sericin extracted silk fibroin fibers in a form of a yarn and
wherein the sericin extracted silk fibroin fibers are substantially non-antigenic.

73. The prosthetic device according to claim 72, wherein the plurality of traverses are organized into a plurality of spaced bundles.

74. The prosthetic device according to claim 72, wherein the at least one knitted section includes two knitted sections, the at least one single continuous fiber extending between the two knitted sections, the two knitted sections being longitudinally separated by an intermediate section defined by the plurality of traverses.

75. The prosthetic device according to claim 74, wherein the intermediate section is less dense than the two knitted sections, the intermediate section providing a shapeable end for the prosthetic device when the prosthetic device is folded transversely across the intermediate section.

76. The prosthetic device according to the claim 75, wherein the intermediate section is tapered the prosthetic device is folded transversely across the intermediate section.

77. The prosthetic device according to claim 72, wherein the at least one single continuous fiber extends beyond the at least one knitted section and forms loops at opposing ends of the prosthetic device.

78. The prosthetic device according to claim 72, further comprising at least one of a knitted sock and a tubular knit section disposed around the at least one knitted section and providing protection against abrasion.

79. The prosthetic device according to claim 72, wherein the at least one knitted section includes a weft-knitted fabric.

80. The prosthetic device according to claim 72, wherein the at least one knitted section includes a warp-knitted fabric.

81. A implantable reconstructive device comprising:
at least one knitted section; and
at least one single continuous fiber traversing the at least one knitted section, the at least one single continuous fiber forming a plurality of traverses extending through the at least one knitted section, and
wherein the at least one knitted section and the at least one single continuous fiber comprise sericin extracted silk fibroin fibers in a form of a yarn and
wherein the sericin extracted silk fibroin fibers are substantially non-antigenic.

82. The implantable reconstructive device according to claim 81, wherein the wherein the at least one knitted section includes two knitted sections, the at least one single continuous fiber extending between the two knitted sections, the two knitted sections being separated by an intermediate section defined by the plurality of traverses.

83. The implantable reconstructive device according to claim 82, wherein the device is shapeable when folded at the intermediate section.

84. The implantable reconstructive device according to claim 83, wherein the shapability of the device facilitates positioning of the device for implantation.

85. The implantable reconstructive device according to claim 82, wherein the device has ends for anchoring.

86. The implantable reconstructive device according to claim 85, wherein once the reconstructive device is anchored the at least one single continuous fiber provides support.

87. The implantable reconstructive device according to claim 82, wherein the silk is *Bombyx mori* silkworm silk fibroin.

88. The implantable reconstructive device according to claim 87, wherein the silk fibroin is a sericin-extracted silk fibroin fiber that substantially retains its native protein structure and has not been dissolved and reconstituted.

89. An implantable support structure comprising:
at least one knitted section formed from a fabric having yarns formed from silk fibers; and
at least one single continuous silk yarn traversing the at least one knitted section, the at least one single continuous silk yarn forming a plurality of traverses extending through the at least one knitted section, and wherein the at least one knitted section and the at least one single continuous fiber comprise sericin extracted silk fibroin fibers in a form of a yarn and
wherein the sericin extracted silk fibroin fibers are substantially non-antigenic.

90. The implantable support structure according to claim 89, wherein the at least one knitted section includes two knitted sections, the at least one single continuous silk yarn extending between the two knitted sections, the two knitted sections being separated by an intermediate section defined by the plurality of traverses.

91. The implantable support structure according to claim 90, wherein the intermediate section is a knitted section comprising a weft yarn.

92. The implantable support structure according to claim 91, wherein the weft yarn traverses the two knitted sections.

93. The implantable support structure according to claim 90, wherein a plurality of traverses extends through the two knitted sections.

94. The implantable support structure according to claim 91, wherein the weft yarn is traversed in a S-shaped or Z-shaped pattern.

95. The implantable support structure according to claim 90, wherein one or more traverses of the single continuous silk yarn is laid or tucked into a single course of the knitted section.

96. The implantable support structure according to claim 95, wherein the tucking effectively locks the continuous yarn into the knitted section.

97. The implantable support structure according to claim 95, wherein the tucked silk yarn is tucked at each knit section.

98. The implantable support structure according to claim 89, wherein the at least one knitted section has a finished edge to prevent unraveling.

99. The implantable support structure according to claim 90, wherein the knitted sections provide scaffolding and void volume for organized tissue in-growth and remodeling.

* * * * *

UNITED STATES PATENT AND TRADEMARK OFFICE
CERTIFICATE OF CORRECTION

| | | |
|---|---|---|
| PATENT NO. | : 8,172,901 B2 | Page 1 of 1 |
| APPLICATION NO. | : 12/052719 | |
| DATED | : May 8, 2012 | |
| INVENTOR(S) | : Gregory H. Altman et al. | |

It is certified that error appears in the above-identified patent and that said Letters Patent is hereby corrected as shown below:

In the Drawings

On sheet 4 of 26, figure 9, line 6, after "UTS" insert -- ) --.

In the Specification

In column 1, line 62-63, delete "autogeneous" and insert -- autogenous --, therefor.

In column 6, line 5, delete "prothestic" and insert -- prosthetic --, therefor.

In column 31, line 49, delete "than" and insert -- then --, therefor.

In column 32, line 20, delete "intrarticular" and insert -- intra-articular --, therefor.

In column 32, line 22, delete "intrarticular" and insert -- intra-articular --, therefor.

In the Claims

In column 34, line 24, in claim 22, delete "section are" and insert -- sections are --, therefor.

In column 35, line 41, in claim 43, delete "in to" and insert -- into --, therefor.

In column 36, line 44, in claim 61, delete "covering" and insert -- knitted covering --, therefor.

In column 38, line 13, in claim 82, after "wherein the" delete "wherein the".

In column 38, line 22, in claim 84, delete "shapability" and insert -- shapeability --, therefor.

Signed and Sealed this
Twentieth Day of May, 2014

Michelle K. Lee
*Deputy Director of the United States Patent and Trademark Office*